US012655136B2

(12) United States Patent
Pfau et al.

(10) Patent No.: US 12,655,136 B2
(45) Date of Patent: Jun. 16, 2026

(54) DIOXANE DERIVATIVES

(71) Applicant: Boehringer Ingelheim International GmbH, Ingelheim am Rhein (DE)

(72) Inventors: Roland Pfau, Mittelbiberach (DE); Georg Dahmann, Biberach an der Riss (DE); Johann Faustus Du Hoffmann, Biberach an der Riss (DE); Kai Gerlach, Mittelbiberach (DE); Riccardo Giovannini, Biberach an der Riss (DE); Christoph Hohn, Freiburg (DE); Stefan Just, Biberach an der Riss (DE); Thorsten Lehmann, Biberach an der Riss (DE); Anton Pekcec, Biberach an der Riss (DE); Julia Schlichtiger, Biberach an der Riss (DE); Heiko Sommer, Warthausen (DE); Christian Specker, Hochdorf (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 306 days.

(21) Appl. No.: 18/384,394

(22) Filed: Oct. 27, 2023

(65) Prior Publication Data

US 2024/0174652 A1 May 30, 2024

(30) Foreign Application Priority Data

Oct. 28, 2022 (EP) .................................... 22204281

(51) Int. Cl.
*A61P 25/18* (2006.01)
*C07D 403/12* (2006.01)
*C07D 405/14* (2006.01)

(52) U.S. Cl.
CPC ............ *C07D 405/14* (2013.01); *A61P 25/18* (2018.01); *C07D 403/12* (2013.01)

(58) Field of Classification Search
CPC .................................................... C07D 405/14
See application file for complete search history.

(56) References Cited

U.S. PATENT DOCUMENTS

2018/0057491 A1 3/2018 Conn et al.

FOREIGN PATENT DOCUMENTS

| | | | |
|---|---|---|---|
| WO | 2004072047 | A1 | 8/2004 |
| WO | 2010033350 | A1 | 3/2010 |
| WO | 2016054491 | A1 | 4/2016 |
| WO | 2016123627 | A1 | 8/2016 |
| WO | 2016123629 | A1 | 8/2016 |
| WO | 2019036534 | A1 | 2/2019 |
| WO | 2019138017 | A1 | 7/2019 |
| WO | 2021028512 | A1 | 2/2021 |

OTHER PUBLICATIONS

Berge S.M., et al., "Pharmaceutical Salts," Journal of Pharmaceutical Science, Jan. 1977, vol. 66, No. 1, pp. 1-19, DOI: 10.1002/jps.2600660104, XP002675560.

Blackshaw L.A., et al., "Metabotropic Glutamate Receptors as Novel Therapeutic Targets on Visceral Sensory Pathways," Frontiers in Neuroscience, Mar. 2011, vol. 5, Article No. 40, pp. 1-7.

Chang H.J., et al., "Metabotropic Glutamate Receptor 4 Expression in Colorectal Carcinoma and its Prognostic Significance," Clinical Cancer Research, May 1, 2005, vol. 11, No. 9, pp. 3288-3295.

Conn P.J., et al., "Pharmacology and Functions of Metabolic Glutamate Receptors," Annual Review of Pharmacology and Toxicology, 1997, vol. 37, pp. 205-237.

Davis M.J., et al., "Role of mGluR4 in Acquisition of Fear Learning and Memory," Neuropharmacology, 2013, vol. 66, pp. 365-372.

International Search Report and Written Opinion for International Application No. PCT/EP2023/080029, dated Feb. 9, 2024, 10 Pages.

International Search Report and Written Opinion for International Application No. PCT/EP2023/084851, dated Feb. 27, 2024, 11 Pages.

International Search Report for International Application No. PCT/EP2023/080028 , dated Feb. 5, 2024, 4 Pages.

Iscru E., et al., "Improved Spatial Learning is Associated with Increased Hippocampal but Not Prefrontal Long-term Potentiation in mGluR4 Knockout Mice," Genes Brain and Behavior, 2013, vol. 12, pp. 615-625.

Isherwood S.N., et al., "Selective and Interactive Effects of D2 Receptor Antagonism and Positive Allosteric mGluR4 Modulation, on Waiting Impulsivity," Neuropharmacology, 2017, vol. 123, pp. 249-260.

Makoff A., et al., "Molecular Characterization and Localization of Human Metabotropic Glutamate Receptor Type 4," Molecular Brain Research, 1996, vol. 37, pp. 239-248.

Marino M.J., et al., "Modulation of Inhibitory Transmission in the Rat Globus Pallidus by Activation of mGluR4," Annals of the New York Academy of Sciences, 2003, vol. 1003, pp. 435-437 (3 Pages).

Nunez-Salces M., et al., "Nutrient-sensing Components of the Mouse Stomach and the Gastric Ghrelin Cell," Neurogastroenterology & Motility, 2020, vol. 32, e13944, pp. 1-13.

Page A., et al., "Peripheral Neural Targets in Obesity," British Journal of Pharmacology, 2012, vol. 166, pp. 1537-1558 (22 Pages).

Schoepp D.D., "Unveiling the Functions of Presynaptic Metabotropic Glutamate Receptors in the Central Nervous System," Journal of Pharmacology and Experimental Therapeutics, 2001, vol. 299, No. 1, pp. 12-20 (9 Pages).

(Continued)

*Primary Examiner* — Yong S. Chong
(74) *Attorney, Agent, or Firm* — David L. Kershner

(57) ABSTRACT

The present invention relates to substituted dioxane derivatives, pharmaceutical compositions containing them and their use in therapy, particularly in the treatment and/or prevention of neuronal and non-neuronal conditions having an association with mGluR4 function and/or in the treatment of obesity by means of mGluR4 modulation.

23 Claims, No Drawings

(56) References Cited

OTHER PUBLICATIONS

Szczurowska E., et al., "Positive Allosteric Modulator of MGluR4 PHCCC Exhibits Proconvulsant Action in Three Models of Epileptic Seizures In Immature Rats," Physiological Research, 2012, vol. 61, pp. 619-628.
Uhera S., et al., "Metabotropic Glutamate Receptor Type 4 is Involved in Autoinhibitor Cascade for Glucagon Secretion by a-cells of Islet of Langerhans," Diabetes, Apr. 2004, vol. 53, pp. 998-1006 (9 Pages).
Unitt J., et al., "Discovery of Small Molecule Human FPR1 Receptor Antagonists," Bioorganic & Medicinal Chemistry Letters, 2011, vol. 21, pp. 2991-2997 (7 Pages).
Written Opinion for International Application No. PCT/EP2023/080028 dated Feb. 5, 2024, 5 Pages.

DIOXANE DERIVATIVES

FIELD OF THE INVENTION

The present invention relates to substituted dioxane derivatives, pharmaceutical compositions containing them and their use in therapy, particularly in the treatment and/or prevention of neuronal and non-neuronal conditions having an association with mGluR4 function and/or in the treatment of obesity by means of mGluR4 modulation.

BACKGROUND OF THE INVENTION

L-glutamate (here referred to as glutamate) is among the most abundant excitatory neurotransmitters within the vertebrate brain. Malfunction of the brain glutamate system often leads to neurological or psychiatric disorders. Therefore, modulation of the glutamatergic system is considered as attractive therapeutic direction.

Glutamate acts via different types of glutamate receptor, which are located on the cell surface. Glutamate receptors include AMPA receptors, kainate receptors, NMDA receptors, and metabotropic glutamate receptors. The metabotropic glutamate receptors (mGluR) exert their action via coupling to G proteins and activation of second messenger systems.

The mGluR subtypes are classified into three groups (distinction by sequence homology, pharmacology, second messenger system) with Group III being the largest group (mGluR4, mGluR6, mGluR7, mGluR8) [Conn and Pin, Annu Rev Pharmacol Toxicol, 1997, 37: 205-237].

Group III mGlu receptors share mainly presynaptic expression Schoepp, Pharmacol Exp Ther, 2001, 299: 12-20) where they modulate glutamatergic as well as GABAergic transmission. Activation of Group III receptors (including mGluR4) reduces transmitter release due to its activation of the Gαi/o which leads to attenuated adenylate cyclase activity.

The mGluR4 receptor is mainly located in presynaptic endings of nerve endings. Expression of mGluR4 has been demonstrated in multiple brain regions with high expression within the basal ganglia and cerebellum among other brain regions. Due to expression of mGluR4 within relevant brain circuitries and its role to modulate transmitter release, mGluR4 modulators are considered to have impact on motor control (including Parkinsons Disease), impulse control, learning and memory, cognition, anxiety, pain, cerebellar functions, epilepsy, modulation of excitation/inhibition balance, which is of crucial importance for information processing (Marino et al. Ann NY Acad Sci, 2003, 1003: 435-437; Isherwood et al. Neuropharmacology 2017, 123: 249-260; Makoff et al. Mol Brain Res, 1996, 37: 239-248; Davis et al. Neuropharmacology 2013, 66: 365-372; Iscru et al. Genes Brain Behav. 2013, 12: 615-625; Szczurowska and Mareš, Physiol Res, 2012, 61: 619-628) but is not limited to these actions.

As mGluR4 has been reported to be also expressed in peripheral tissue like islets of Langerhans, it is considered that antagonists of mGluR4 function may also have therapeutic effect in disorders including but not limited to metabolic disorders, gastro-intestinal disorders, and cancer (Chang et al. Clin Cancer Res. 2005, 11: 3288-3295; Uhera et al. Diabetes 2004, 53: 998-1006; Nunez-Salces et al. Neurogastroenterol Motil 2020, 32).

As mGluR4 has been reported to be also expressed in vagal afferents as well as within central satiety pathways and brain circuits, but not limited to, it is considered that antagonists of mGluR4 function may also have therapeutic effect in disorders including but not limited to overweight and obesity (Blackshow et al. Front Neurosci 2011, 5: 40; 1-7; Page et al. Br J Pharmacol. 2012, 166: 1537-1558).

WO21028512 describes arylsulfonamides as mGluR4 NAMs. However, the activity of those compounds seems too low to be applicable as a drug, especially so since acidic arylsulfonamides might additionally be subject to efflux at the blood brain barrier, which limits their brain exposure for CNS applications.

DETAILED DESCRIPTION OF THE INVENTION

The present invention provides novel substituted dioxane derivatives that unexpectedly are potent mGluR4 negative modulators.

Compounds of the present invention are potent mGluR4 negative modulators inhibiting the function of mGluR4 thereby blocking glutamate induced intracellular cAMP lowering.

The present invention thus provides compounds for use in the treatment of a mGluR4 mediated disorder.

The present invention further provides methods of treating a mGluR4 mediated disorder in a human subject comprising administering to the subject a compound or composition of a compound of the present invention or a pharmaceutically acceptable salt thereof.

In one aspect, the invention relates to a method for treating a condition for which reduced mGluR4 activity can reduce the severity of the condition, by administering a compound inhibiting mGluR4 function, such as a compound as described herein that inhibits glutamate induced intracellular cAMP lowering. Described herein are compounds, which are antagonists of mGluR4 function that have a measured 1050 for inhibition of mGluR4 of 100 nanomolar, preferred 50 nM or less.

In another aspect, the compounds described herein, which are antagonists of mGluR4 function can be used to inhibit a function of mGluR4, for example a mGluR4-mediated glutamate induced intracellular cAMP lowering. In some embodiments, the compounds described herein can be used to inhibit a mGluR4 mediated glutamate induced intracellular cAMP lowering in vitro, for example 5 in cells in culture. In other embodiments, the compounds described herein can be used to inhibit a mGluR4 mediated glutamate induced intracellular cAMP lowering in vivo.

Definitions

Terms not specifically defined herein should be given the meanings that would be given to them by one skilled in the art in the light of the disclosure and the context.

The terms “negative modulator”, “antagonist” and “inhibitor” are used interchangeably to refer to an agent that decreases or suppresses a biological activity such as the reduction of an activity of a receptor, and comprise negative allosteric modulators (NAM). mGluR4 receptors as described herein include homomultimeric and heteromultimeric structures (e.g. homomultimeric mGluR4 and heteromeric mGluR4-mGluR2). Inhibitors of mGluR4 function include inhibitors having any combination of the structural and/or functional properties disclosed herein.

An “effective amount” of a (mGluR4) antagonist, with respect to the subject methods of inhibition or treatment, refers to an amount of the antagonist in a preparation which, when applied as part of a desired dosage regimen brings about a desired clinical or functional result. Without being bound by theory, an effective amount of a mGluR4 antagonist for use in the methods of the present invention includes an amount of a mGluR4 antagonist effective to decrease one or more in vitro or in vivo functions of a mGluR4 receptor. Exemplary functions include, but are not limited to, changed intracellular cAMP, or synaptic transmitter release, or changed neuronal activity or modulation of impulsive behavior. Compounds that antagonize mGluR4 function include compounds that antagonize an in vitro or in vivo functional activity of mGluR4. When a particular functional activity is only readily observable in an in vitro assay, the ability of a compound to inhibit mGluR4 function in that in vitro assay serves as a reasonable proxy for the activity of that compound. In certain embodiments, an effective amount is an amount sufficient to inhibit a mGluR4-mediated cellular function.

The mGluR4 antagonists for use in the methods of the present invention may be characterized according to their activity, or lack of activity, against one or more receptors. When other receptors are referred to, inhibition of a function of such other receptors is defined similarly. For example, inhibition of a receptor or an activity of a receptor means the antagonist inhibits one or more functional activities of the other receptor. Such functions include, for example, signal transduction across a cellular membrane and/or changes in the intracellular concentration of intracellular substances like cAMP mediated by the particular receptor and subsequent functions like e.g. neurotransmitter release. The terms "compound" and "agent" are used interchangeably to refer to the negative modulators of the invention.

In the groups, radicals, or moieties defined below, the number of carbon atoms is often specified preceding the group, for example, C1-6-alkyl means an alkyl group or radical having 1 to 6 carbon atoms. In general, for groups comprising two or more subgroups, the last named subgroup is the radical attachment point, for example, the substituent "aryl-C1-3-alkyl-" means an aryl group which is bound to a C1-3-alkyl-group the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

Stereochemistry/Solvates/Hydrates

The compounds described herein can be chiral (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Resolution of racemic mixtures of compounds can be carried out by any of numerous methods known in the art. An example method includes fractional recrystallizaion using a "chiral resolving agent" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S- and R-forms, or diastereomerically pure forms), 2-phenylglycinol, norephedrine, ephedrine, N-methylephedrine, cyclohexylethylamine, and 1,2-diaminocyclohexane.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms, such as keto-enol tautomers.

Unless specifically indicated, throughout the specification and the appended claims, a given chemical formula or name shall encompass tautomers and all stereo, optical and geometrical isomers (e.g. enantiomers, diastereoisomers, E/Z isomers) and racemates thereof, as well as mixtures in different proportions of the separate enantiomers, mixtures of diastereoisomers, or mixtures of any of the foregoing forms where such isomers and enantiomers exist.

Compounds of the invention can also include all isotopes of atoms occurring in the intermediates or final compounds. For example, the compound of the invention may be radiolabeled with radioactive isotopes, such as for example tritium ($^3H$) or carbon-14 ($^{14}C$). All isotopic variations, whether radioactive or not, are intended to be encompassed within the scope of the present invention.

Salts

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid. Also included are the salts of amino acids such as arginate, and salts of organic acids like glucuronic or galactunoric acids (see, for example, Berge et al., "Pharmaceutical Salts", Journal of Pharmaceutical Science, 1977, 66, 1-19).

The neutral form of the compounds of the invention is preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The terms "mGluR4", "mGluR4 protein", and "mGluR4 receptor" are used interchangeably throughout the application. Unless expressly stated, the term mGluR4 includes homomultimeric structures (e.g. homomultimeric mGluR4) and heteromultimeric structures (e.g. heteromultimeric mGluR4-mGluR2).

Biological Assays

The biological activity of compounds is determined by the following methods:

A. In Vitro Testing of mGluR4 Potency The in vitro activity of the compounds according to the invention may be investigated as follows:

The HEK293 cell overexpressing the human metabotropic Glutamate 4 receptor are thawed at 37° C. and immediately diluted with cell culture medium. After centrifugation, the cell pellet is re-suspended in medium and then distributed from a stirred spinner flask into the wells of the assay plate. The plates are incubated for one hour at room temperature before they are incubated for 24 hours at 37° C./5% CO2. After washing the cells in the plate three times with 80 uL HBSS/HEPES buffer (10 uL buffer remained in the wells after washing), 5 uL per well of compounds diluted in HBSS/HEPES buffer containing 0.2% BSA (final concentration: 0.1%) and 1 mM IBMX (final concentration: 0.5 mM) are added to the wells of the assay plate. Thereafter 5 uL per well of L-Glutamic acid (final concentration: 10 uM), forskolin (final concentration: 1 uM) and 1 mM IBMX (final concentration: 0.5 mM) dissolved in HBSS/HEPES buffer containing 0.2% BSA (final concentration: 0.1%) are added to the assay plate (final DMSO concentration: 1%). Several wells of the assay plate are used either for the positive and the negative controls or for the cAMP standard curve. The assay plate is incubated for 30 minutes at room temperature. Then 5 ul per well of Anti-cAMP-Antibody-d2 solution and 5 ul per well of cAMP-Europium Cryptate dilution are added to all wells of the plate and the plate is incubated another 60 minutes light protected at room temperature. The emission at 615 nm and 665 nm (Excitation wavelength: 320 nm) are measured on the EnVision™ reader (Perkin Elmer). The ratio between the emission at 665 nm and 615 is calculated by the reader. The whole assay is performed in the dark or under green light.

The cAMP standard is prepared by diluting the cAMP stock solution with HBSS/Hepes buffer: 5 µl/well of the cAMP dilutions (in HBSS/Hepes buffer containing 1 mM IBMX and 0.2% BSA—final concentration: 0.5 mM IBMX and 0.1% BSA) are added to 10 ul/well HBSS/Hepes buffer plus 5 ul/well 4% DMSO in HBSS/Hepes containing 0.2% BSA (final DMSO concentration: 1% —like in the wells containing compounds) in the wells of the assay plate. The final cAMP concentrations in the assay plate are: 0, 0.17, 0.69, 2.78, 11.1, 44.5, 178, and 712 nM (two wells/cAMP concentration).

Each assay microtiter plate contained also wells with vehicle controls instead of compound as controls for L-Glutamic acid induced signal (negative control; 100% CTL; 10 uM L-Glutamic acid+1 uM forskolin+0.5 mM IBMX+1% DMSO) and wells with vehicle controls without L-Glutamic acid as controls for non-specific changes in signal (positive control; 0% CTL; 0 uM L-Glutamic acid+1 uM forskolin+0.5 mM IBMX+1% DMSO).

The analysis of the data is performed by the calculation the ratio between the emission at 665 nm and the emission at 615 nm (Em665/Em615 ratio). Thereafter the signals of the compounds are normalized using the positive and negative controls by the following formula:

$$PoC=100\times((\text{Signal Sample}-\text{Positive Control})/(\text{Negative Control}-\text{Positive Control}))$$

B. Assessment of Metabolic Stability in Human Liver Microsomes (Human MST)

The metabolic stability of the compounds according to the invention may be investigated as follows:

The metabolic degradation of the test compound is assayed at 37° C. with pooled human liver microsomes. The final incubation volume of 100 µL per time point contains TRIS buffer pH 7.6 at room temperature (0.1 M), MgCl 2 (5 mM), microsomal protein (1 mg/mL) and the test compound at a final concentration of 1 µM. Following a short preincubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life ($t_{1/2}$) is determined by the slope of the semi-logarithmic plot of the concentration-time profile.

C. Assessment of Efflux in Madin-Darby Canine Kidney (MDCK) Cells Transfected with the Human MDR1 Gene Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable.

MDCK-MDR1 cells (1-2x10e5 cells/1 cm2 area) are seeded on filter inserts (Costar transwell polycarbonate or PET filters, 0.4 µm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$), 4.17 mM $NaHCO_3$, 1.19 mM $Na_2HPO_4\times7H_2O$, 0.41 mM $NaH_2PO_4\times$ H2O, 15 mM HEPES, 20 mM glucose, 0.25% BSA, pH 7.4) to prepare the transport solutions (0.1-300 µM compound, final DMSO<=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

D. Assessment of Efficacy on Impulsive Behavior Tested in the Rat Five Choice Serial Reaction Time Task 5-CSRTT Assessment of efficacy on motor impulsive behavior may be investigated as follows:

5-CSRTT task training took place according to standard protocols (Isherwood et al. Neuropharmacology 2017, 123: 249-260). Briefly, rats were trained to nose poke at the location of a light cue presented at 1 of 5 locations on a curved wall of an operant box (Med Associates Inc, St. Albans, Vermont). If a nose poke occurred at the illuminated location during or up to 1 s after stimulus presentation a sugar pellet was delivered in a reward receptacle located across the chamber. Infrared beams in each choice aperture and the reward receptacle allowed for precise detection of the rat at this task associated operanda. Motor impulsive behavior was defined as a response at any nose poke aperture which occurred before onset of the light cue (premature response).

After reaching stable performance, a new analytical approach was applied which revealed trait-like (long-term) stability in the number of premature responses individual animals made across several months. In general, this analysis made it possible to robustly stratify animals into high- and low-impulsive groups based on longitudinal assessment of the number of premature responses they made during training.

Experiments were performed in cross-over such that all experiment subjects received both vehicle and compound, on separate days, with each administration separated by ~2 weeks. The order of vehicle and compound administration was randomized within experimental subjects, while a third group was administered Atomoxetine on both experimental days as a technical control.

As a standardized numerical threshold for impulsivity levels, animals with >40 and <40 premature responses (out of 200 initiated trials) in vehicle were labeled as high and low impulsive, respectively. Importantly, this numerical threshold-based labeling overlapped >80% with the longitudinal analysis of the training data (described above). The high convergence of these two approaches towards stratification allowed us to robustly compare compound effects in stably high- vs stably low-impulsive rats in the 5-CSRTT.

Biological Data

TABLE 1

In vitro potencies of the structurally closest compounds disclosed in WO2019/138017 (as determined in Assay A)

| Example | Structure | Assay A mGluR4 IC50 |
|---|---|---|
| Example 8 in WO2019/138017 | 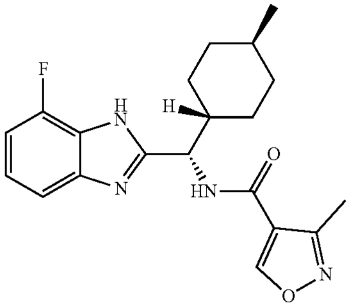 [SMILES: Cc1nocc1C(=O)N[C@H](c1nc2cccc(F)c2[nH]1)[C@H]1CC[C@H](C)CC1] | 9.85 μM |

TABLE 1-continued

In vitro potencies of the structurally closest compounds disclosed in WO2019/138017 (as determined in Assay A)

| Example | Structure | Assay A mGluR4 IC50 |
|---|---|---|
| Example 12 in WO2019/138017 | 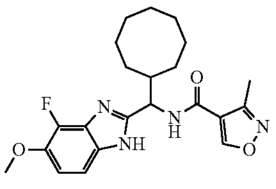 [SMILES: COc1ccc2[nH]c(C(NC(=O)c3conc3C)C3CCCCCCC3)nc2c1F] | >10 μM |
| Example 125 in WO2019/138017 | 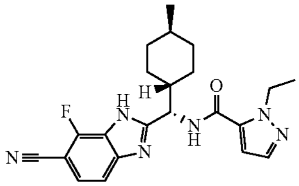 [SMILES: CCn1nccc1C(=O)N[C@H](c1nc2ccc(C#N)c(F)c2[nH]1)[C@H]1CC[C@H](C)CC1] | 5.6 μM |
| Intermediate 250 in WO2019/138017 (regioisomere 1) | 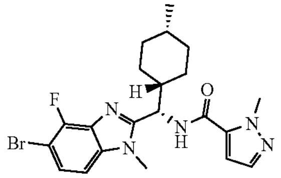 [SMILES: Cn1nccc1C(=O)N[C@H](c1nc2c(F)c(Br)ccc2n1C)[C@H]1CC[C@@H](C)CC1] | 6.3 μM |
| Intermediate 250 in WO2019/138017 (regioisomere 2) | 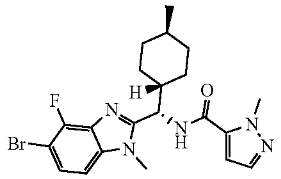 [SMILES: Cn1nccc1C(=O)N[C@H](c1nc2c(F)c(Br)ccc2n1C)[C@H]1CC[C@H](C)CC1] | 4.0 μM |

Compounds of the present invention differ structurally from the structurally closest compounds in the prior art (i.e. Examples 8, 12, 125 and Intermediate 250 in WO 2019/138017) in that the heteromonocycle bound as an carboxamide is a pyrazine (6-membered heteroaryl) group rather than a pyrazole or isoxazole moiety (5-membered heteroaryl). Whereas the structurally closest compounds disclosed in WO2019/138017 are as disclosed therein immunomodulators (IL-17 modulators), compounds of the present invention unexpectedly are highly potent mGluR4 negative modulators (see Table 2). The structurally closest compounds disclosed in WO2019/138017 were tested in Assay A and found to have no therapeutically relevant activity as mGluR4 modulators (Table 1). Unexpectedly, compounds of the present invention are >100 times more potent in Assay A. (Compare data in Tables 1 and 2).

TABLE 2

In vitro potencies of compounds of the present invention as determined in Assay A

| Example | Structure | Assay A mGluR4 $IC_{50}$ [uM] |
|---|---|---|
| 1 | 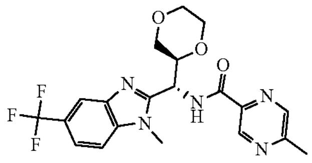 [SMILES: Cc1cnc(C(=O)N[C@H](c2nc3cc(C(F)(F)F)ccc3n2C)[C@H]2COCCO2)cn1] | 0.020 |
| 1-1 | 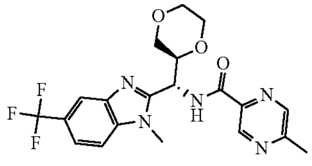 [SMILES: Cc1cnc(C(=O)N[C@H](c2nc3cc(C(F)(F)F)ccc3n2C)[C@H]2COCCO2)cn1] | 0.067 |
| 2 | 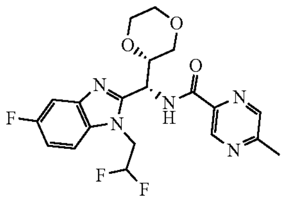 [SMILES: Cc1cnc(C(=O)N[C@H](c2nc3cc(F)ccc3n2CC(F)F)[C@H]2COCCO2)cn1] | 0.014 |
| 3 | 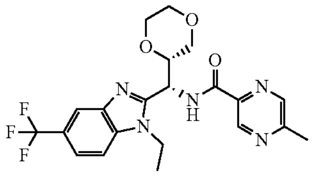 [SMILES: CCn1c([C@@H](NC(=O)c2cnc(C)cn2)[C@H]2COCCO2)nc2cc(C(F)(F)F)ccc21] | 0.005 |
| 4 | 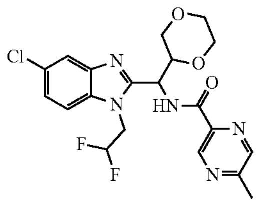 [SMILES: Cc1cnc(C(=O)NC(c2nc3cc(Cl)ccc3n2CC(F)F)C2COCCO2)cn1] | 0.007 |
| 5 | 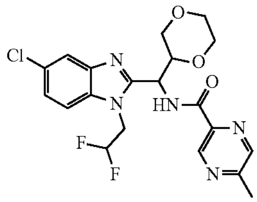 [SMILES: Cc1cnc(C(=O)NC(c2nc3cc(Cl)ccc3n2CC(F)F)C2COCCO2)cn1] | 0.062 |
| 6 | 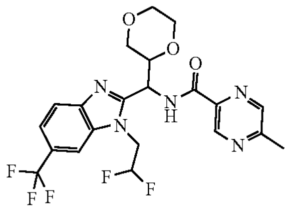 [SMILES: Cc1cnc(C(=O)NC(c2nc3ccc(C(F)(F)F)cc3n2CC(F)F)C2COCCO2)cn1] | 0.006 |

TABLE 2-continued

In vitro potencies of compounds of the present invention as determined in Assay A

| Example | Structure | Assay A mGluR4 $IC_{50}$ [uM] |
|---|---|---|
| 7 | 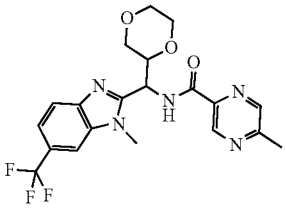 [SMILES: Cc1cnc(C(=O)NC(c2nc3ccc(C(F)(F)F)cc3n2C)C2COCCO2)cn1] | 0.07 |
| 8 | 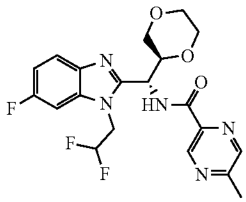 [SMILES: Cc1cnc(C(=O)N[C@H](c2nc3ccc(F)cc3n2CC(F)F)[C@H]2COCCO2)cn1] | 0.031 |
| 9 | 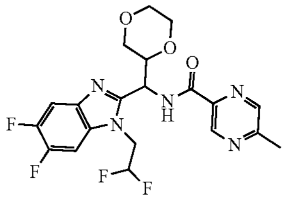 [SMILES: Cc1cnc(C(=O)NC(c2nc3cc(F)c(F)cc3n2CC(F)F)C2COCCO2)cn1] | 0.011 |
| 10 | 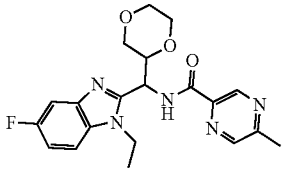 [SMILES: CCn1c(C(NC(=O)c2cnc(C)cn2)C2COCCO2)nc2cc(F)ccc21] | 0.020 |
| 11 | 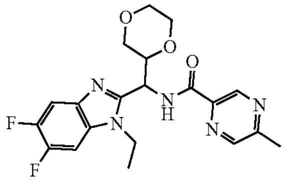 [SMILES: CCn1c(C(NC(=O)c2cnc(C)cn2)C2COCCO2)nc2cc(F)c(F)cc21] | 0.015 |

Use in Treatment/Method of Use

The present invention is directed to compounds which are useful in the treatment and/or prevention of a disease, disorder and condition wherein the inhibition of mGluR4 activity is of therapeutic benefit, including but not limited to the treatment of psychiatric and neurological conditions associated with impulse control deficits or maladaptive impulsivity. Such impulse control deficits are seen in addictions including substance use disorders; personality disorders such as borderline personality disorder, antisocial personality disorder, conduct disorder, eating disorders such as binge eating disorder, attention deficit hyperactivity disorder, bipolar disorder, stress related disorders such as post-traumatic stress disorder, tic disorders like Toureett's syndrome, other movement disorders such as restless legs syndrome. According to a further aspect of the invention, compounds of the present invention are useful in the treatment of mGluR4 related pathophysiological disturbances, cognition, motivated behaviours/reward, mood and stress, aggression. In addition, there is therapeutic benefit in cancer and related disorders associated with maladaptive tumorgenesis like osteosarcoma. According to a further aspect of the invention, compounds of the present invention are useful in the treatment of metabolic disorders by mGluR4-related modulation of satiety pathways and/or signaling, to treat disorders including but not limited to obesity.

In view of their pharmacological effect, compounds of the present invention are suitable for use in the treatment and/or prevention of a disease or condition selected from the list consisting of (1) Disorders associated with malfunction in impulse control such as pathological gambling, trichotillomania, intermittent explosive disorder, conduct disorder, antisocial personality disorder, kleptomania, pyromania, compulsive shopping, internet addiction, sexual compulsion, sexual disorder, sexual dysfunction, psychosexual disorder, eating disorders, such as binge eating, bulimia nervosa, anorexia nervosa, other specified feeding or eating disorders, obesity, overweight, cachexia, appetite/taste disorders, vomiting, nausea, Prader-Willi-syndrome, hyperphagia, appetite/taste disorders, bipolar disorder, post-traumatic stress disorder;

(2) Substance abuse/dependence/seeking or addiction as well as relapse prevention (including but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics;

(3) Psychiatric and neurological conditions like attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la, restless legs syndrome, dementia, dyskinesia, severe mental retardation, neurodegenerative disorders including nosological entities such as disinhibition-dementia-parkinsonism-amyotrophy complex, pallido-ponto-nigral degeneration, Mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder, neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders including but not limited to Tourette Syndrome and other movement disorders, dpilepsia, chronic pain;

(4) Cognitive dysfunction in psychiatric or neurological disorder, cognitive impairments associated with schizophrenia, Alzheimer's disease and other neurological and psychiatric disorders;

(5) Personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders;

(6) sleep disorders such as narcolepsy, jetlag, sleep apnea, insomnia, parasomnia, disturbed biological and circadian rhythms, sleep disturbances associated with psychiatric and neurological disorders;

(7) Non-neuronal conditions including metabolic conditions like diabetes, insulin resistance, metabolic syndrome, overweight, obesity, as well as use for weight reduction, cosmetic weight loss, relapse prevention during or after obesity treatment, body weight maintenance, emesis, disorders associated with malfunction of the cardiovascular-vascular system and disorders associated with maladaptive blood pressure control like hypertension or hypotension; (8) Cancer and related disorders associated with maladaptive tumorgenesis like osteosarcoma, breast cancer, ependymoma, bladder cancer, colorectal cancer.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Combination Therapy Compounds according to the present invention can be combined with other treatment options known to be used in the art in connection with a treatment of any of the indications the treatment of which is in the focus of the present invention.

Among such active pharmaceutical ingredients or treatment options that are considered suitable for combination with the compounds and the treatment according to the present invention are antidepressants, mood stabilizers, typical and atypical antipsychotics, anxiolytics, antiepileptic drugs, anti-Parkinsons medication, sleeping agents, cognitive enhancers, stimulants, medication for attention deficit hyperactivity disorder, additional psychoactive drugs, anti-inflammatory drugs, analgesic drugs, chemotherapeutic drugs, as well as combination with treatment options used for metabolic disorders, liver diseases and kidney diseases.

EXPERIMENTAL SECTION

List of Abbreviations:

% Sol percentage of solvent
µL microliter
ACN acetonitrile
AcOH acetic acid
aq. aqueous
Boc tert.-butyloxycarbonyl
$Boc_2O$ di-tert.-butyl-dicarbonate
chir. chiral
CIP 2-chloro-1,3-dimethyl-2-imidazolinium hexafluorophosphate
conc. concentrated
d day
DA diode Array
DAD diode array detector
DCM dichloromethane
DMF N,N-dimethylformamide
ELSD Evaporative Light Scattering Detector
EtOAc ethyl acetate ETOH ethanol
g gram
h hour
half-conc. half concentrated
HPLC high performance liquid chromatography
i. vac. in vacuo
IPA Isopropylic Alcohol
M molar
MeOH methanol
MEOH methanol
mg milligram
min minute
ml milliliter
mL milliliter
MS Mass Spectrometer
N normal
NBS N-bromo-succinimide
NMM N-methyl-morpholine
NMP N-Methylpyrrolidone
PE petrolether
PPA 1-propanephosphonic acid cyclic anhydride
prep. Preparative
PSI pound per square inch
quant. quantitative
Rf retarding front
RT retention time
sat. saturated
scCO2 supercritical carbon dioxide
SFC supercritical fluid chromatography
TBTU O-(Benzotriazol-1-yl)-N,N,N,N-tetramethyluronium-tetrafluoroborat
TEA triethylamine
Temp. temperature
tert. tertiary
TFA trifluoroacetic acid
THF tetrahydrofuran
wt weight
X-Phos G1 Chloro-(2-dicyclohexylphosphino-2',4',6'-triisopropyl-1,1'-biphenyl)[2-(2-aminoethyl)-phenyl)]-palladium(II)

Methods:

HPLC-MS Methods:

Method A

| | |
|---|---|
| Method Name: | Z003_S05 |
| Device description: | Agilent 1200 with DA- and MS-Detector |
| Column: | XBridge C18_3.0 × 30 mm_2.5 μm |
| Column producer: | Waters |
| Description: | |

| Gradient/Solvent Time [min] | % Sol [Water 0.1% $NH_3$] | % Sol [Acetonitrile] | Flow [ml/min] | Temp [° C.] | Back pressure [PSI] |
|---|---|---|---|---|---|
| 0.0 | 95.0 | 5.0 | 2.2 | 60.0 | |
| 0.2 | 95.0 | 5.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Method B

| | |
|---|---|
| Method Name: | Z011_S03 |
| Device description: | Agilent 1200 with DA- and MS-Detector |
| Column: | XBridge C18_3.0 × 30 mm_2.5 μm |
| Column producer: | Waters |
| Description: | |

| Gradient/Solvent Time [min] | % Sol [Water 0.1% $NH_3$] | % Sol [Acetonitrile] | Flow [ml/min] | Temp [° C.] | Back pressure [PSI] |
|---|---|---|---|---|---|
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

| Method C | | | | | |
|---|---|---|---|---|---|
| Method Name: | Z018_S04 | | | | |
| Device description: | Agilent 1200 with DA- and MS-Detector | | | | |
| Column: | Sunfire C18_3.0 × 30 mm_2.5 μm | | | | |
| Column producer: | Waters | | | | |
| Description: | | | | | |
| Gradient/Solvent Time [min] | % Sol [Water 0.1% TFA] | % Sol [Acetonitrile] | Flow [ml/min] | Temp [° C.] | Back pressure [PSI] |
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Chiral SFC Analytical Methods:

| Method 1: | | | | | |
|---|---|---|---|---|---|
| Method Name: | G_IG_IPA_NH3_002 | | | | |
| Device description: | Agilent 1260 Infinity II SFC with DAD | | | | |
| Column: | Chiralpak ® IG_3 × 100 mm_3 μm | | | | |
| Column producer: | Daicel | | | | |
| Description: | | | | | |
| Gradient/Solvent Time [min] | % Sol [$scCO_2$] | % Sol [IPA 20 mM NH3] | Flow [ml/min] | Temp [° C.] | Back pressure [PSI] |
| 0.0 | 95.0 | 5.0 | 2.0 | 40.0 | 2175.0 |
| 3.6 | 40.0 | 60.0 | 2.0 | 40.0 | 2175.0 |
| 4.0 | 40.0 | 60.0 | 2.0 | 40.0 | 2175.0 |

| Method 2: | | | | | |
|---|---|---|---|---|---|
| Method Name: | G_SB_IPA_NH3_001 | | | | |
| Device description: | Agilent 1260 SFC with DAD and MS | | | | |
| Column: | CHIRAL ART ® Cellulose SB_4.6 × 250 mm_5 μm | | | | |
| Column producer: | YMC | | | | |
| Description: | | | | | |
| Gradient/Solvent Time [min] | % Sol [$scCO_2$] | % Sol [IPA 20 mM NH3] | Flow [ml/min] | Temp [° C.] | Back pressure [PSI] |
| 0.0 | 95.0 | 5.0 | 4.0 | 40.0 | 2175.0 |
| 9.0 | 40.0 | 60.0 | 4.0 | 40.0 | 2175.0 |
| 10.0 | 40.0 | 60.0 | 4.0 | 40.0 | 2175.0 |

| Method 3: | | | | | |
|---|---|---|---|---|---|
| Method Name: | G_SC_MEOH_NH3_001 | | | | |
| Device description: | Agilent 1260 SFC with DAD and MS | | | | |
| Column: | CHIRAL ART ® Cellulose SC_4.6 × 250 mm_5 μm | | | | |
| Column producer: | YMC | | | | |
| Description: | | | | | |
| Gradient/Solvent Time [min] | % Sol [$scCO_2$] | % Sol [MEOH 20 mM NH3] | Flow [ml/min] | Temp [° C.] | Back pressure [PSI] |
| 0.0 | 95.0 | 5.0 | 4.0 | 40.0 | 2175.0 |
| 9.0 | 40.0 | 60.0 | 4.0 | 40.0 | 2175.0 |
| 10.0 | 40.0 | 60.0 | 4.0 | 40.0 | 2175.0 |

| Method 4: | | | | | |
|---|---|---|---|---|---|
| Method Name: | I_AC_10_IPA_NH3_002 | | | | |
| Device description: | Agilent 1260 Infinity II SFC with DAD | | | | |
| Column: | CHIRAL ART ® Amylose-C Neo_3 × 100 mm_3 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

| Method 5: | | | | | |
|---|---|---|---|---|---|
| Method Name: | I_AC_15_IPA_NH3_002 | | | | |
| Device description: | Agilent 1260 Infinity II SFC with DAD | | | | |
| Column: | CHIRAL ART ® Amylose-C Neo_3 × 100 mm_3 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85.0 | 15.0 | 2.0 | 40.0 | 2175.0 |
| 4.0 | 85.0 | 15.0 | 2.0 | 40.0 | 2175.0 |

| Method 6: | | | | | |
|---|---|---|---|---|---|
| Method Name: | I_AC_20_IPA_NH3_002 | | | | |
| Device description: | Agilent 1260 Infinity II SFC with DAD | | | | |
| Column: | CHIRAL ART ® Amylose-C Neo_3 × 100 mm_3 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 2.0 | 40.0 | 2175.0 |
| 4.0 | 80.0 | 20.0 | 2.0 | 40.0 | 2175.0 |

| Method 7: | | | | | |
|---|---|---|---|---|---|
| Method Name: | I_ADH_15_IPA_NH3_001 | | | | |
| Device description: | Agilent 1260 SFC with DAD and ELSD | | | | |
| Column: | Chiralpak ® AD-H_4.6 × 250 mm_5 μm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85.0 | 15.0 | 4.0 | 40.0 | 2175.0 |
| 10.0 | 85.0 | 15.0 | 4.0 | 40.0 | 2175.0 |

Method 8:

| | |
|---|---|
| Method Name: | I_C2_10_MEOH_NH3_002 |
| Device description: | Agilent 1260 Infinity II SFC with DAD |
| Column: | Lux(R) Cellulose-2_3 × 100 mm_3 µm |
| Column producer: | Phenomenex |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 9:

| | |
|---|---|
| Method Name: | I_C2_15_IPA_NH3_001 |
| Device description: | Agilent 1260 SFC with DAD and ELSD |
| Column: | Lux ® Cellulose-2_4.6 × 250 mm_5 µm |
| Column producer: | Phenomenex |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 10:

| | |
|---|---|
| Method Name: | I_C2_15_MEOH_NH3_001 |
| Device description: | Agilent 1260 SFC with DAD and ELSD |
| Column: | Lux ® Cellulose-2_4.6 × 250 mm_5 µm |
| Column producer: | Phenomenex |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 11:

| | |
|---|---|
| Method Name: | I_C2_15_MEOH_NH3_002 |
| Device description: | Agilent 1260 Infinity II SFC with DAD |
| Column: | Lux(R) Cellulose-2_3 × 100 mm_3 µm |
| Column producer: | Phenomenex |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 2.0 | 40.0 | 2175.0 |
| 4.0 | 85.0 | 15.0 | 2.0 | 40.0 | 2175.0 |

| Method 12: | | | | | |
|---|---|---|---|---|---|
| Method Name: | I_C2__20__IPA__NH3__001 | | | | |
| Device description: | Agilent 1260 SFC with DAD and ELSD | | | | |
| Column: | Lux ® Cellulose-2__4.6 × 250 mm__5 μm | | | | |
| Column producer: | Phenomenex | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

| Method 13: | | | | | |
|---|---|---|---|---|---|
| Method Name: | I_C2__20__IPA__NH3__002 | | | | |
| Device description: | Agilent 1260 Infinity II SFC with DAD | | | | |
| Column: | Lux(R) Cellulose-2__3 × 100 mm__3 μm | | | | |
| Column producer: | Phenomenex | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 2.0 | 40.0 | 2175.0 |
| 4.0 | 80.0 | 20.0 | 2.0 | 40.0 | 2175.0 |

| Method 14: | | | | | |
|---|---|---|---|---|---|
| Method Name: | I_C2__20__MEOH__NH3__002 | | | | |
| Device description: | Agilent 1260 Infinity II SFC with DAD | | | | |
| Column: | Lux(R) Cellulose-2__3 × 100 mm__3 μm | | | | |
| Column producer: | Phenomenex | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 80.0 | 20.0 | 2.0 | 40.0 | 2175.0 |
| 4.0 | 80.0 | 20.0 | 2.0 | 40.0 | 2175.0 |

| Method 15: | | | | | |
|---|---|---|---|---|---|
| Method Name: | I_C4__10__MEOH__NH3__002 | | | | |
| Device description: | Agilent 1260 Infinity II SFC with DAD | | | | |
| Column: | Lux(R) Cellulose-4__3 × 100 mm__3 μm | | | | |
| Column producer: | Phenomenex | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

| Method 16: | | | | | |
|---|---|---|---|---|---|
| Method Name: | I_IA__10__ETOH__NH3__001 | | | | |
| Device description: | Agilent 1260 SFC with DAD and MS | | | | |
| Column: | Chiralpak ® IA__4.6 × 250 mm__5 μm | | | | |
| Column producer: | Daicel | | | | |
| Description: | | | | | |

| Gradient/Solvent Time [min] | % Sol [scCO2] | % Sol [ETOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| Method 17: | | | | | |
|---|---|---|---|---|---|
| Method Name: | I_IA__10__MEOH__NH3__001 | | | | |
| Device description: | Agilent 1260 SFC with DAD and MS | | | | |
| Column: | Chiralpak ® IA__4.6 × 250 mm__5 μm | | | | |
| Column producer: | Daicel | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| Method 18: | | | | | |
|---|---|---|---|---|---|
| Method Name: | I_IA__15__MEOH__NH3__001 | | | | |
| Device description: | Agilent 1260 SFC with DAD and MS | | | | |
| Column: | Chiralpak ® IA__4.6 × 250 mm__5 μm | | | | |
| Column producer: | Daicel | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 19: | | | | | |
|---|---|---|---|---|---|
| Method Name: | I_IA__25__MEOH__NH3__001 | | | | |
| Device description: | Agilent 1260 SFC with DAD and MS | | | | |
| Column: | Chiralpak ® IA__4.6 × 250 mm__5 μm | | | | |
| Column producer: | Daicel | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

| Method 20: | | | | | |
|---|---|---|---|---|---|
| Method Name: | I_IA__30__IPA__NH3__001 | | | | |
| Device description: | Agilent 1260 SFC with DAD and MS | | | | |
| Column: | Chiralpak ® IA__4.6 × 250 mm__5 μm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 70.0 | 30.0 | 4.0 | 40.0 | 2175.0 |
| 10.0 | 70.0 | 30.0 | 4.0 | 40.0 | 2175.0 |

| Method 21: | | | | | |
|---|---|---|---|---|---|
| Method Name: | I_IBN__15__IPA__NH3 | | | | |
| Device description: | Agilent 1260 SFC with DAD and MS | | | | |
| Column: | Chiralpak ® IB N__4.6 × 250 mm__5 μm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85.0 | 15.0 | 4.0 | 40.0 | 2175.0 |
| 10.0 | 85.0 | 15.0 | 4.0 | 40.0 | 2175.0 |

| Method 22: | | | | | |
|---|---|---|---|---|---|
| Method Name: | I_IC__20__MEOH__NH3__001 | | | | |
| Device description: | Agilent 1260 SFC with DAD and MS | | | | |
| Column: | Chiralpak ® IC__4.6 × 250 mm__5 μm | | | | |
| Column producer: | Daicel | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

| Method 23: | | | | | |
|---|---|---|---|---|---|
| Method Name: | I_IG__10__IPA__NH3__002 | | | | |
| Device description: | Agilent 1260 Infinity II SFC with DAD | | | | |
| Column: | Chiralpak ® IG__3 × 100 mm__3 μm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

| Method 24: | | | | | |
|---|---|---|---|---|---|
| Method Name: | I_IG__10__MEOH__NH3__002 | | | | |
| Device description: | Agilent 1260 Infinity II SFC with DAD | | | | |
| Column: | Chiralpak ® IG__3 × 100 mm__3 μm | | | | |
| Column producer: | Daicel | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

| Method 25: | | | | | |
|---|---|---|---|---|---|
| Method Name: | I_IG__15__IPA__NH3__001 | | | | |
| Device description: | Agilent 1260 SFC with DAD and MS | | | | |
| Column: | Chiralpak ® IG__4.6 × 250 mm__5 μm | | | | |
| Column producer: | Daicel | | | | |
| Description: | | | | | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 26: | | | | | |
|---|---|---|---|---|---|
| Method Name: | I_IG__15__IPA__NH3__002 | | | | |
| Device description: | Agilent 1260 Infinity II SFC with DAD | | | | |
| Column: | Chiralpak ® IG__3 × 100 mm__3 μm | | | | |
| Column producer: | Daicel | | | | |
| Description: | | | | | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 2.0 | 40.0 | 2175.0 |
| 4.0 | 85.0 | 15.0 | 2.0 | 40.0 | 2175.0 |

| Method 27: | | | | | |
|---|---|---|---|---|---|
| Method Name: | I_IG__15__MEOH__NH3__001 | | | | |
| Device description: | Agilent 1260 SFC with DAD and MS | | | | |
| Column: | Chiralpak ® IG__4.6 × 250 mm__5 μm | | | | |
| Column producer: | Daicel | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 28:

| | |
|---|---|
| Method Name: | I_IG_20_IPA_NH3_001 |
| Device description: | Agilent 1260 SFC with DAD and MS |
| Column: | Chiralpak ® IG_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 29:

| | |
|---|---|
| Method Name: | I_IG_20_MEOH_NH3_001 |
| Device description: | Agilent 1260 SFC with DAD and MS |
| Column: | Chiralpak ® IG_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 30:

| | |
|---|---|
| Method Name: | I_IG_25_MEOH_NH3_001 |
| Device description: | Agilent 1260 SFC with DAD and MS |
| Column: | Chiralpak ® IG_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method 31:

| | |
|---|---|
| Method Name: | I_IG_30_IPA_NH3_001 |
| Device description: | Agilent 1260 SFC with DAD and MS |
| Column: | Chiralpak ® IG_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

| Method 32: | |
|---|---|
| Method Name: | I_IG_35_MEOH_NH3_001 |
| Device description: | Agilent 1260 SFC with DAD and MS |
| Column: | Chiralpak ® IG_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 65.0 | 35.0 | 4.0 | 40.0 | 2175.0 |
| 10.0 | 65.0 | 35.0 | 4.0 | 40.0 | 2175.0 |

| Method 33: | |
|---|---|
| Method Name: | I_SA_05_IPA_NH3_001 |
| Device description: | Agilent 1260 SFC with DAD and MS |
| Column: | CHIRAL ART ® Amylose SA_4.6 × 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 95.0 | 5.0 | 4.0 | 40.0 | 2175.0 |
| 10.0 | 95.0 | 5.0 | 4.0 | 40.0 | 2175.0 |

| Method 34: | |
|---|---|
| Method Name: | I_SA_10_IPA_NH3_001 |
| Device description: | Agilent 1260 SFC with DAD and MS |
| Column: | CHIRAL ART ® Amylose SA_4.6 × 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| Method 35: | |
|---|---|
| Method Name: | I_SA_10_MEOH_NH3_001 |
| Device description: | Agilent 1260 SFC with DAD and MS |
| Column: | CHIRAL ART ® Amylose SA_4.6 × 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| Method 36: | | | | | |
|---|---|---|---|---|---|
| Method Name: | I_SA_15_IPA_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85.0 | 15.0 | 4.0 | 40.0 | 2175.0 |
| 10.0 | 85.0 | 15.0 | 4.0 | 40.0 | 2175.0 |

| Method 37: | | | | | |
|---|---|---|---|---|---|
| Method Name: | I_SA_15_MEOH_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 85.0 | 15.0 | 4.0 | 40.0 | 2175.0 |
| 10.0 | 85.0 | 15.0 | 4.0 | 40.0 | 2175.0 |

| Method 38: | | | | | |
|---|---|---|---|---|---|
| Method Name: | I_SA_20_IPA_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

| Method 39: | | | | | |
|---|---|---|---|---|---|
| Method Name: | I_SA_20_MEOH_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

| Method 40: | | | | | |
|---|---|---|---|---|---|
| Method Name: | I_SA_25_IPA_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 75.0 | 25.0 | 4.0 | 40.0 | 2175.0 |
| 10.0 | 75.0 | 25.0 | 4.0 | 40.0 | 2175.0 |

| Method 41: | | | | | |
|---|---|---|---|---|---|
| Method Name: | I_SA_25_MEOH_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 75.0 | 25.0 | 4.0 | 40.0 | 2175.0 |
| 10.0 | 75.0 | 25.0 | 4.0 | 40.0 | 2175.0 |

| Method 42: | | | | | |
|---|---|---|---|---|---|
| Method Name: | I_SA_35_MEOH_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 65.0 | 35.0 | 4.0 | 40.0 | 2175.0 |
| 10.0 | 65.0 | 35.0 | 4.0 | 40.0 | 2175.0 |

| Method 43 | | | | | |
|---|---|---|---|---|---|
| Method Name: | I_SB_10_IPA_NH3_001 | | | | |
| Device description: | Agilent 1260 SFC with DAD and MS | | | | |
| Column: | CHIRAL ART ® Cellulose SB_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

| Method 44: | |
|---|---|
| Method Name: | I_SB_10_MEOH_NH3_001 |
| Device description: | Agilent 1260 SFC with DAD and MS |
| Column: | CHIRAL ART ® Cellulose SB_4.6 × 250 mm_5 µm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| Method 45: | |
|---|---|
| Method Name: | I_SB_15_IPA_NH3_001 |
| Device description: | Agilent 1260 SFC with DAD and MS |
| Column: | CHIRAL ART ® Cellulose SB_4.6 × 250 mm_5 µm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 46: | |
|---|---|
| Method Name: | I_SB_15_MEOH_NH3_001 |
| Device description: | Agilent 1260 SFC with DAD and MS |
| Column: | CHIRAL ART ® Cellulose SB_4.6 × 250 mm_5 µm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 47: | |
|---|---|
| Method Name: | I_SB_20_MEOH_NH3_001 |
| Device description: | Agilent 1260 SFC with DAD and MS |
| Column: | CHIRAL ART ® Cellulose SB_4.6 × 250 mm_5 µm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

| Method 48: | | | | | |
|---|---|---|---|---|---|
| Method Name: | I_SB_25_IPA_NH3_001 | | | | |
| Device description: | Agilent 1260 SFC with DAD and MS | | | | |
| Column: | CHIRAL ART ® Cellulose SB_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 75.0 | 25.0 | 4.0 | 40.0 | 2175.0 |
| 10.0 | 75.0 | 25.0 | 4.0 | 40.0 | 2175.0 |

| Method 49: | | | | | |
|---|---|---|---|---|---|
| Method Name: | I_SC_05_IPA_NH3_001 | | | | |
| Device description: | Agilent 1260 SFC with DAD and MS | | | | |
| Column: | CHIRAL ART ® Cellulose SC_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 95.0 | 5.0 | 4.0 | 40.0 | 2175.0 |
| 10.0 | 95.0 | 5.0 | 4.0 | 40.0 | 2175.0 |

| Method 50: | | | | | |
|---|---|---|---|---|---|
| Method Name: | I_SC_10_IPA_NH3_001 | | | | |
| Device description: | Agilent 1260 SFC with DAD and MS | | | | |
| Column: | CHIRAL ART ® Cellulose SC_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

| Method 51: | | | | | |
|---|---|---|---|---|---|
| Method Name: | I_SC_10_IPA_NH3_002 | | | | |
| Device description: | Agilent 1260 Infinity II SFC with DAD | | | | |
| Column: | CHIRAL ART ® Cellulose-SC_3 × 100 mm_3 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

Method 52:

| | |
|---|---|
| Method Name: | I_SC_10_MEOH_NH3_001 |
| Device description: | Agilent 1260 SFC with DAD and MS |
| Column: | CHIRAL ART ® Cellulose SC_4.6 × 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Method 53:

| | |
|---|---|
| Method Name: | I_SC_10_MEOH_NH3_002 |
| Device description: | Agilent 1260 Infinity II SFC with DAD |
| Column: | CHIRAL ART ® Cellulose-SC_3 × 100 mm_3 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 54:

| | |
|---|---|
| Method Name: | I_SC_15_IPA_NH3_001 |
| Device description: | Agilent 1260 SFC with DAD and MS |
| Column: | CHIRAL ART ® Cellulose SC_4.6 × 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 55:

| | |
|---|---|
| Method Name: | I_SC_15_MEOH_NH3_001 |
| Device description: | Agilent 1260 SFC with DAD and MS |
| Column: | CHIRAL ART ® Cellulose SC_4.6 × 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 56: | | | | | |
|---|---|---|---|---|---|
| Method Name: | I_SC_20_IPA_NH3_001 | | | | |
| Device description: | Agilent 1260 SFC with DAD and MS | | | | |
| Column: | CHIRAL ART ® Cellulose SC_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

| Method 57: | | | | | |
|---|---|---|---|---|---|
| Method Name: | I_SC_20_MEOH_NH3_001 | | | | |
| Device description: | Agilent 1260 SFC with DAD and MS | | | | |
| Column: | CHIRAL ART ® Cellulose SC_4.6 × 250 mm_5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

| Method 58: | | | | | |
|---|---|---|---|---|---|
| Method Name: | I_SC_25_IPA_NH3_001 | | | | |
| Device description: | Agilent 1260 SFC with DAD and MS | | | | |
| Column: | CHIRAL ART ® Cellulose SC_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 75.0 | 25.0 | 4.0 | 40.0 | 2175.0 |
| 10.0 | 75.0 | 25.0 | 4.0 | 40.0 | 2175.0 |

| Method 59: | | | | | |
|---|---|---|---|---|---|
| Method Name: | I_SC_25_MEOH_NH3_001 | | | | |
| Device description: | Agilent 1260 SFC with DAD and MS | | | | |
| Column: | CHIRAL ART ® Cellulose SC_4.6 × 250 mm_5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 75.0 | 25.0 | 4.0 | 40.0 | 2175.0 |
| 10.0 | 75.0 | 25.0 | 4.0 | 40.0 | 2175.0 |

| Method 60: | | | | | |
|---|---|---|---|---|---|
| Method Name: | I_SC_30_IPA_NH3_001 | | | | |
| Device description: | Agilent 1260 SFC with DAD and MS | | | | |
| Column: | CHIRAL ART ® Cellulose SC_4.6 × 250 mm_5 μm | | | | |
| Column producer: | YMC | | | | |
| Description: | | | | | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

| Method 61: | | | | | |
|---|---|---|---|---|---|
| Method Name: | I_SJ_10_IPA_NH3_001 | | | | |
| Device description: | Agilent 1260 SFC with DAD and MS | | | | |
| Column: | CHIRAL ART ® Cellulose SJ_4.6 × 250 mm_5 μm | | | | |
| Column producer: | YMC | | | | |
| Description: | | | | | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 10.0 | 90.0 | 10.0 | 2.0 | 40.0 | 2175.0 |

| Method 62: | | | | | |
|---|---|---|---|---|---|
| Method Name: | I_SZ_10_MEOH_NH3_003 | | | | |
| Device description: | Agilent 1260 Infinity II SFC with DAD and MS | | | | |
| Column: | CHIRAL ART ® Cellulose SZ_4.6 × 250 mm_5 μm | | | | |
| Column producer: | YMC | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| Method 63: | | | | | |
|---|---|---|---|---|---|
| Method Name: | I_SC_15_MEOH_NH3_003 | | | | |
| Device description: | Agilent 1260 Infinity II SFC with DAD and MS | | | | |
| Column: | CHIRAL ART ® Cellulose SC_4.6 × 250 mm_5 μm | | | | |
| Column producer: | YMC | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 64: | | | | | |
|---|---|---|---|---|---|
| Method Name: | I_SC_10_IPA_NH3_003 | | | | |
| Device description: | Agilent 1260 Infinity II SFC with DAD and MS | | | | |
| Column: | CHIRAL ART ® Cellulose SC_4.6 × 250 mm_5 µm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

| Method 65: | | | | | |
|---|---|---|---|---|---|
| Method Name: | I_IG_30_MEOH_NH3_002 | | | | |
| Device description: | Agilent 1260 Infinity II SFC with DAD and MS | | | | |
| Column: | CHIRAL ART ® Cellulose SC_4.6 × 250 mm_5 µm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 70.0 | 30.0 | 2.0 | 40.0 | 2175.0 |
| 4.0 | 70.0 | 30.0 | 2.0 | 40.0 | 2175.0 |

| Method 63: | | | | | |
|---|---|---|---|---|---|
| Method Name: | I_IG_35_IPA_NH3_003 | | | | |
| Device description: | Agilent 1260 Infinity II SFC with DAD | | | | |
| Column: | Chiralpak ® IG_4.6 × 250 mm_5 µm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 65.0 | 35.0 | 4.0 | 40.0 | 2175.0 |
| 10.0 | 65.0 | 35.0 | 4.0 | 40.0 | 2175.0 |

| Method 64: | | | | | |
|---|---|---|---|---|---|
| Method Name: | I_IG_20_IPA_NH3_003 | | | | |
| Device description: | Agilent 1260 Infinity II SFC with DAD | | | | |
| Column: | Chiralpak ® IG_4.6 × 250 mm_5 µm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

| Method 65: | |
|---|---|
| Method Name: | I_IH_05_MEOH_NH3_003 |
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 95.0 | 5.0 | 4.0 | 40.0 | 2175.0 |
| 10.0 | 95.0 | 5.0 | 4.0 | 40.0 | 2175.0 |

| Method 66: | |
|---|---|
| Method Name: | I_IH_10_IPA_NH3_003 |
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| Method 67: | |
|---|---|
| Method Name: | I_IG_15_MEOH_NH3_003 |
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 68: | |
|---|---|
| Method Name: | I_IG_15_IPA_NH3_003 |
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 69: | | | | | |
|---|---|---|---|---|---|
| Method Name: | I_IG_20_MEOH_NH3_002 | | | | |
| Device description: | Agilent 1260 Infinity II SFC with DAD | | | | |
| Column: | Chiralpak ® IG_3 × 100 mm_3 μm | | | | |
| Column producer: | Daicel | | | | |
| Description: | | | | | |
| Gradient/Solvent Time [min] | % Sol [scCO2] | % Sol [MEOH20 mM NH3] | Flow [ml/min] | Temp [° C.] | Back pressure [PSI] |
| 0.0 | 80 | 20 | 2.0 | 40.0 | 2175.0 |
| 4.0 | 80 | 20 | 2.0 | 40.0 | 2175.0 |

| Method 70: | | | | | |
|---|---|---|---|---|---|
| Method Name: | I_SB_10_IPA_NH3_003 | | | | |
| Device description: | Agilent 1260 Infinity II SFC with DAD | | | | |
| Column: | CHIRAL ART ® Cellulose SB_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90 | 10 | 4.0 | 40.0 | 2175.0 |
| 10.0 | 90 | 10 | 4.0 | 40.0 | 2175.0 |

| Method 71 | | | | | |
|---|---|---|---|---|---|
| Method Name: | I_SC_15_IPA_NH3_003 | | | | |
| Device description: | Agilent 1260 Infinity II SFC with DAD | | | | |
| Column: | CHIRAL ART ® Cellulose SB_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85 | 15 | 4.0 | 40.0 | 2175.0 |
| 10.0 | 85 | 15 | 4.0 | 40.0 | 2175.0 |

| Method 72 | | | | | |
|---|---|---|---|---|---|
| Method Name: | I_SZ_20_MEOH_NH3_003 | | | | |
| Device description: | Agilent 1260 Infinity II SFC with DAD | | | | |
| Column: | CHIRAL ART ® Cellulose SB_4.6 × 250 mm_5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 80 | 20 | 4.0 | 40.0 | 2175.0 |
| 10.0 | 80 | 15 | 4.0 | 40.0 | 2175.0 |

| Method 73 | | | | | |
|---|---|---|---|---|---|
| Method Name: | I_C4__20__MEOH__NH3__002 | | | | |
| Device description: | Agilent 1260 Infinity II SFC with DAD | | | | |
| Column: | Lux(R) Cellulose-4__3 × 100 mm__3 μm | | | | |
| Column producer: | Phenomenex | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80 | 20 | 2.0 | 40.0 | 2175.0 |
| 10.0 | 80 | 20 | 2.0 | 40.0 | 2175.0 |

| Method 74 | | | | | |
|---|---|---|---|---|---|
| Method Name: | I_IG__25__IPA__NH3__002 | | | | |
| Device description: | Agilent 1260 Infinity II SFC with DAD | | | | |
| Column: | Chiralpak ® IG__3 × 100 mm__3 μm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 75 | 25 | 2.0 | 40.0 | 2175.0 |
| 4.0 | 75 | 25 | 2.0 | 40.0 | 2175.0 |

| Method 75 | | | | | |
|---|---|---|---|---|---|
| Method Name: | I_SC__20__IPA__NH3__003 | | | | |
| Device description: | Agilent 1260 Infinity II SFC with DAD and MS | | | | |
| Column: | CHIRAL ART ® Cellulose SC__4.6 × 250 mm__5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80 | 20 | 4.0 | 40.0 | 2175.0 |
| 10.0 | 80 | 20 | 4.0 | 40.0 | 2175.0 |

| Method 76 | | | | | |
|---|---|---|---|---|---|
| Method Name: | I_SB10__20__MEOH__NH3__003 | | | | |
| Device description: | Agilent 1260 Infinity II SFC with DAD and MS | | | | |
| Column: | CHIRAL ART ® Cellulose SC__4.6 × 250 mm__5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 90 | 10 | 4.0 | 40.0 | 2175.0 |
| 10.0 | 90 | 10 | 4.0 | 40.0 | 2175.0 |

Method 77

| | |
|---|---|
| Method Name: | I_C4__25__IPA__NH3__002 |
| Device description: | Agilent 1260 Infinity II SFC with DAD |
| Column: | Lux(R) Cellulose-4__3 × 100 mm__3 μm |
| Column producer: | Phenomenex |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 75 | 25 | 2.0 | 40.0 | 2175.0 |
| 4.0 | 75 | 25 | 2.0 | 40.0 | 2175.0 |

Method 78

| | |
|---|---|
| Method Name: | I_SB__15__MEOH__NH3__002 |
| Device description: | Agilent 1260 Infinity II SFC with DAD |
| Column: | CHIRAL ART ® Cellulose SC__3 × 100 mm__3 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 2.0 | 40.0 | 2175.0 |
| 4.0 | 85.0 | 15.0 | 2.0 | 40.0 | 2175.0 |

Method 79

| | |
|---|---|
| Method Name: | I_AC__10__IPA__NH3__002 |
| Device description: | Agilent 1260 Infinity II SFC with DAD |
| Column: | CHIRAL ART ® Amylose-C Neo__3 × 100 mm__3 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 80

| | |
|---|---|
| Method Name: | I_IA__10__ETOH__NH3__001 |
| Device description: | Agilent 1260 SFC with DAD and MS |
| Column: | Chiralpak ® IA__4.6 × 250 mm__5 μm |
| Column producer: | Daicel |
| Description: | |

| Gradient/Solvent Time [min] | % Sol [scCO2] | % Sol [ETOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| Method 81 | | | | | |
|---|---|---|---|---|---|
| Method Name: | I_C4_10_MEOH_NH3_002 | | | | |
| Device description: | Agilent 1260 Infinity II SFC with DAD | | | | |
| Column: | Lux(R) Cellulose-4_3 × 100 mm_3 μm | | | | |
| Column producer: | Phenomenex | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

| Method 82 | | | | | |
|---|---|---|---|---|---|
| Method Name: | I_SA_10_MEOH_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | YMC | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

| Method 83 | | | | | |
|---|---|---|---|---|---|
| Method Name: | I_IA_10_ETOH_NH3_001 | | | | |
| Device description: | Agilent 1260 SFC with DAD and MS | | | | |
| Column: | Chiralpak ® IA_4.6 × 250 mm_5 μm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 2.0 | 40.0 | 2175.0 |
| 4.0 | 80.0 | 20.0 | 2.0 | 40.0 | 2175.0 |

| Method 84 | | | | | |
|---|---|---|---|---|---|
| Method Name: | I_AC_20_IPA_NH3_002 | | | | |
| Device description: | Agilent 1260 Infinity II SFC with DAD | | | | |
| Column: | CHIRAL ART ® Amylose-C Neo_3 × 100 mm_3 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 2.0 | 40.0 | 2175.0 |
| 4.0 | 80.0 | 20.0 | 2.0 | 40.0 | 2175.0 |

| Method 85 | | | | | |
|---|---|---|---|---|---|
| Method Name: | I_C4_10_MEOH_NH3_002 | | | | |
| Device description: | Agilent 1260 Infinity II SFC with DAD | | | | |
| Column: | Lux(R) Cellulose-4_3 × 100 mm_3 μm | | | | |
| Column producer: | Phenomenex | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

| Method 86 | | | | | |
|---|---|---|---|---|---|
| Method Name: | I_SZ_10_IPA_NH3_003 | | | | |
| Device description: | Agilent 1260 Infinity II SFC with DAD and MS | | | | |
| Column: | CHIRAL ART ® Cellulose SZ_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

| Method 87 | | | | | |
|---|---|---|---|---|---|
| Method Name: | I_C2_10_MEOH_NH3_002 | | | | |
| Device description: | Agilent 1260 Infinity II SFC with DAD | | | | |
| Column: | Lux(R) Cellulose-2_3 × 100 mm_3 μm | | | | |
| Column producer: | Phenomenex | | | | |
| Description: | | | | | |
| Gradient/Solvent Time [min] | % Sol [scCO2] | % Sol [MEOH20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

| Method 88 | | | | | |
|---|---|---|---|---|---|
| Method Name: | I_SA_15_MEOH_NH3_001 | | | | |
| Device description: | Agilent 1260 SFC with DAD and MS | | | | |
| Column: | CHIRAL ART ® Amylose SA_4.6 × 250 mm_5 μm | | | | |
| Column producer: | CHIRAL ART ® Amylose SA_4.6 × 250 mm_5 μm | | | | |
| Description: | YMC | | | | |
| Gradient/Solvent Time [min] | % Sol [scCO2] | % Sol [MEOH20 mM NH3] | Flow [ml/min] | Temp [° C.] | Back pressure [PSI] |
| 0.0 | 85.0 | 15.0 | 4.0 | 40.0 | 2175.0 |
| 10.0 | 85.0 | 15.0 | 4.0 | 40.0 | 2175.0 |

| Method 89 | | | | | |
|---|---|---|---|---|---|
| Method Name: | I_IG_10_MEOH_NH3_002 | | | | |
| Device description: | Agilent 1260 Infinity II SFC with DAD | | | | |
| Column: | Chiralpak ® IG_3 × 100 mm_3 μm | | | | |
| Column producer: | Daicel | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

| Method 90 | | | | | |
|---|---|---|---|---|---|
| Method Name: | I_SB_05_IPA_NH3_002 | | | | |
| Device description: | Agilent 1260 Infinity II SFC with DAD | | | | |
| Column: | CHIRAL ART ® Cellulose-SB_3 × 100 mm_3 μm | | | | |
| Column producer: | YMC | | | | |
| Description: | | | | | |

| Gradient/Solvent Time [min] | % Sol [scCO2] | % Sol [IPA20 mM NH3] | Flow [ml/min] | Temp [° C.] | Back pressure [PSI] |
|---|---|---|---|---|---|
| 0.0 | 95.0 | 5.0 | 2.0 | 40.0 | 2175.0 |
| 4.0 | 95.0 | 5.0 | 2.0 | 40.0 | 2175.0 |

NMR method: NMR spectra were recorded on a Bruker AVANCE IIIHD 400 MHz instrument using TopSpin 3.2 pl6 software. Chemical shifts are given in parts per million (ppm) downfield from an internal reference like trimethylsilane and/or water and/or solvent (eg. d6-DMSO) in δ units. Selected data are reported in the following manner: chemical shift (multiplicity, coupling constants (J), number of hydrogens). Abbreviations are as follows: s (singlet), d (doublet), t (triplet), q (quartet), spt (septet), m (multiplet), br (broad).

EXAMPLES

Example 1

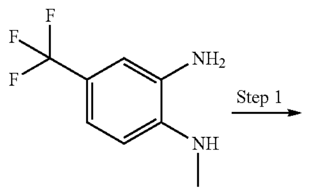

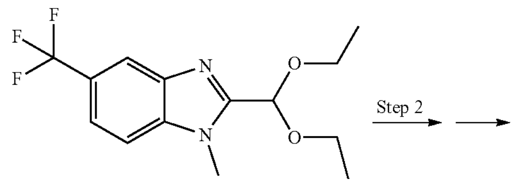

Int-1a

-continued

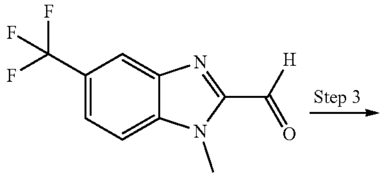

Int-1b

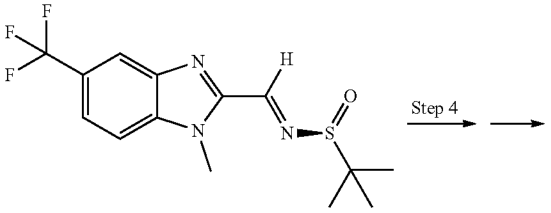

Int-1c

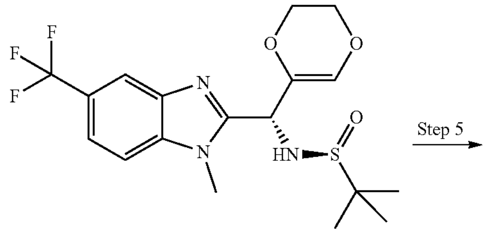

Int-1d

-continued

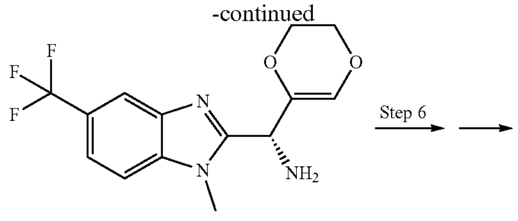

Int-1e

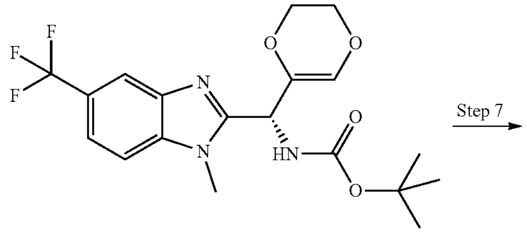

Int-1f

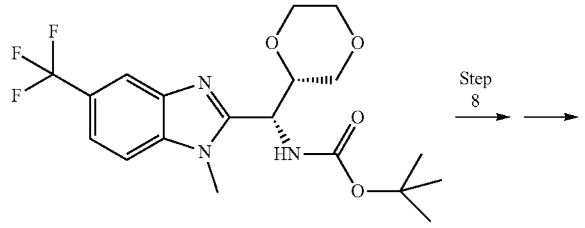

Int-1g

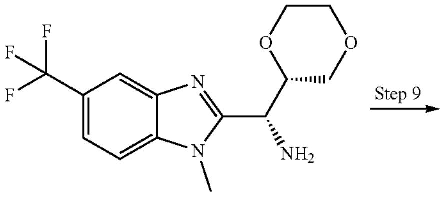

Int-1h

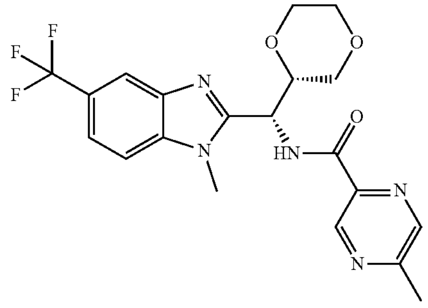

Example 1, 1-1

Step 1:

Sodium (0.95 g, 41.2 mmol) is given into 80 mL EtOH and the mixture cooled to not exceed 35° C. and stirred for 45 min. N1-methyl-4-(trifluoromethyl)-benzene-1,2-diamine (2.50 g, 12.9 mmol) and ethyl diethoxy acetate (4.15 mL, 23.2 mmik) in 20 mL EtOH are added, and the mixture heated to reflux for 20 h. Then, 200 mL sat. aq. $NH_4CL$ are added, the mixture is concentrated i. vac., the residue diluted with 250 mL water and extracted with ethyl acetate. The combined organic layers are dried over $MgSO_4$ and concentrated i. vac. The residue is taken up in THF/MeOH and purified by column chromatography (XBridge C18, 10 μm, eluent gradient: ($H_2O$+0.15% $NH_3$): ACN: 56:44→36:64). Product containing fractions are combined and freeze-dried. The solid was taken up in DCM and concentrated i. vac.

Yield: 1.78 g (5.89 mmol; 46%) Int-1a

MS (ESL): $(M+H)^+$303; HPLC: RT=1.05 min, Method: Z011_S03

Step 2:

A mixture from Int-la (12.8 g, 42.3 mmol) and hydrochloric acid in dioxane (4N; 128 mL, 512 mmol) is stirred and heated to reflux for 1.5 h. Heating was removed and the mixture poured into a mixture of 800 mL water with 500 mL sat. aq. $NaHCO_3$ solution. The mixture is stirred for 5 min and filtered. The solid is washed with water and dried i. vac., the residue is taken up in n-butyl acetate and concentrated i. vac.

Yield: 9.33 g (40.1 mmol; 95%) Int-1 b

MS (ESL): $(M+H)^+$229; HPLC: RT=0.88 min, Method: Z011_S03

Step 3:

Int-1b (23.2 g, 99.6 mmol), (S)-(−)-2-methyl-2-propanesulfinamide (13.3 g, 105 mmol) and $Cs_2CO_3$ (42.2 g, 130 mmol) in 370 mL DCM are stirred under heating and reflux for 1.25 h. Then heating is removed, $MgSO_4$ is added, the mixture filtrated and the filtrate concentrated i. vac. The residue is taken up in DCM and di-isopropyl ether and concentrated i. vac. The forming solid is filtrated and collected. The filtrate is further concentrated i. vac. and the residue purified via column chromatography (silica gel; eluent gradient: petroleum ether: EtOAc: 80:20→45:55). The product containing fractions are combined and concentrated i. vac. The residue is combined with the collected solid.

Yield: 31.6 g (95.4 mmol; 96%) Int-1c

MS (ESL): $(M+H)^+$332; HPLC: RT=1.07 min, Method: Z018_S04

Chiral SFC Rt 4.27 min (Method: I_SA_10_IPA_NH3_003)

Step 4:

Under argon atmosphere and in extra dried glassware, 1-4 dioxene (17.18 mL, 211.25 mmol) in 150 mL THF is cooled to −35° C. and n-hexyl lithium (2.45N in hexane; 76.98 mL, 188.52 mmol) is added with the temperature staying below −30° C. Then cooling is removed, and the mixture warmed to 20° C. The mixture is cooled immediately to 0° C. and stirred at this temperature for 30 min. Then the mixture is cooled to −65° C. and added to a mixture of Int-1c (50 g, 150.89 mmol) in 500 mL THF at −75° C. under argon in extra dried glassware in a way to keep the temperature of the mixture below −70° C. Afterwards the mixture is stirred at −70° C. for 20 min. Then the mixture is poured into 650 mL sat. aq. $NH_4Cl$ solution. tert.butyl methyl ether (650 ml) is added and the mixture warmed to room temperature under stirring. The aq. layer is extracted with tert. butyl methyl ether, the combined organic layers washed with brine, dried over $MgSO_4$ and concentrated i. vac. To the residue EtOAc (70 ml) is added. The mixture is filtrated and washed with EtOAc, the solid is collected. The obtained product contained only one stereoisomer.

Yield: 38,5 g (92 mmol; 61%) Int-1d. Chiral SFC Rt 5.38 min (Method: I_IH_15_IPA_NH3_003)

Step 5:

To Int-1d (15.4 g, ~90%, 33.2 mmol) in 347 mL MeOH at 10° C. is added hydrogen chloride in dioxane (4N, 18.3 mL, 73.0 mmil). The cooling is removed after 5 min and the mixture stirred for 22 h at ambient temperature. Then conc. aq. $NH_3$ solution is added to adjust the pH to 7.5 and the mixture concentrated i. vac. The residue is adjusted to pH 8 by addition of conc. aq. $NH_3$ solution, 300 mL water are added and the mixture is extracted with DCM. The aq. layer is adjusted to pH 10 by addition of $Na_2CO_2$ solution (aq., 2N) and extracted with EtOAc. The organic layers are washed with water, combined, dried over $MgSO_4$ and concentrated i. vac.

Yield: 12.4 g (content ~75%; 29.8 mmol; 90%) Int-1e

MS ($ESI^+$): (M+H)+314; HPLC: RT=0.87 min, Method: Z011_503

Chiral SFC Rt 3.51 min (Method: I_IG_20_1 PA_NH3_003)

Step 6:

To Int-1 e (12.4 g, ~75%, 29.8 mmol) in 250 mL DCM with TEA (8.8 mL, 63.3 mmol) is added $Boc_2O$ (8.3 g, 38.0 mmol) and the mixture stirred at ambient temperature for 15.5 h. The organic layer is washed with water, dried over $MgSO_4$ and concentrated i. vac. Then it is purified via chromatography (silica gel, eluent gradient: petroleum ether: EtOAc 75:25→45:55). The product containing fractions are combined and concentrated i. vac.

Yield: 9.82 g (23.7 mmol; 75%) Int-1f. MS ($ESI^+$): $(M+H)^+$414

Chiral SFC Rt 4.64 min (Method: I_IG_10_1 PA_NH3_003)

Step 7:

Int-1f (8.8 g, 21.3 mmol) in 300 mL THF is mixed with palladium on charcoal (10%, 1.3 g) and the mixture hydrogenated under a hydrogen atmosphere at 60 psi for 22 h, then further palladium on charcoal is added (10%, 1 g), hydrogenation is continued for 5 h, then additional palladium on charcoal is added (10%, 0.5 g) and hydrogenation is continued for 3 h. The mixture is allowed to stay overnight, then it is filtered and concentrated i. vac. The product is obtained as a mixture of stereosisomers, which is used further without separation. Only the major isomer is depicted in the synthesis scheme. Yield: 8.76 g (21.1 mmol; 99%) Int-1 g MS ($ESI^+$): $(M+H)^+$ 416; HPLC: RT=1.04 min, Method: Z011_503

Stereoisomer 1: Chiral SFC Rt 2.69 min (Method: I_IG_10_IPA_NH3_003)

Stereoisomer 2: Chiral SFC Rt 3.33 min (Method: I_IG_10_IPA_NH3_003)

Step 8:

TFA (14.3 mL, 186 mmol) is added to Int-1 g (7.7 g, 18.7 mmol) in 65 mL DCM at 5° C. Cooling is removed and the mixture stirred for 3.8 h at ambient temperature. 150 g ice is added and the mixture adjusted to pH ~10 by addition of conc. aq. $NH_3$ solution. The aqueous layer is extracted with DCM, the combined organic layers dried over $MgSO_4$ and concentrated i. vac.

Yield: 5.92 g (18.7 mmol; quant.) Int-1 h

Chiral SFC Rt 2.57 min (Method: I_SA_10_MEOH_NH3_003)Step 9:

To a mixture of Int-1 h (5.9 g, 18.7 mmol) with NMM (5.1 mL, 46.8 mmol) in 59 mL EtOAc is added 5-methylpyraine-2-carboxylic acid (3.2 g, 22.6 mmol) and the mixture cooled to 0° C. under stirring. Then PPA (50% in EtOAc; 14.5 mL, 24.3 mmol) is added dropwise while keeping the temperature below 10° C. Cooling is removed after 5 min and the mixture stirred at ambient temperature for 75 min. Water is added and the mixture adjusted to pH 9 by adding NMM. The aq. layer is extracted with EtOAc, the combined organic layers washed with half-conc. brine, charcoal added, stirred and dried over $MgSO_4$. After filtration the mixture is concentrated i. vac., the residue taken up in EtOAc and purified via chromatography (silica gel, eluent: EtOAc: EtOH 97:3). The product containing fractions are combined and concentrated i. vac. The product is obtained as a mixture of two stereoisomers, which is purified by chiral SFC.

Yield: 4.05 g (9.30 mmol) example 1 and 0.71 g (1.63 mmol) example 1-1

Example 1: N-[(R)-[(2S)-1,4-dioxan-2-yl][1-methyl-5-(trifluoromethyl)-1H-1,3-benzodiazol-2-yl]methyl]-5-methylpyrazine-2-carboxamide

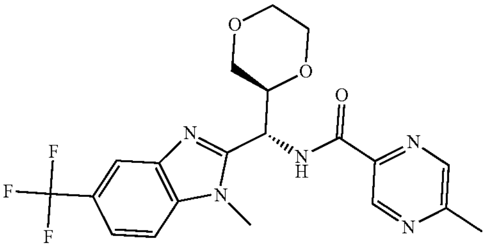 [SMILES: Cc1cnc(C(=O)N[C@H](c2nc3cc(C(F)(F)F)ccc3n2C)[C@H]2COCCO2)cn1]

HPLC-MS; Method: Z018_S04; $R_t$ [min]: 0.94 — MS: 436 $(M + H)^+$

Chiral SFC Rt Method: I_C2_20_MEOH_NH3_002 — Rt [min]: 1.37

$^1H$ NMR (400 MHz, DMSO-$d_6$) δ ppm 2.61 (s, 3 H) 3.31 - 3.39 (m, 1 H) 3.41 - 3.50 (m, 1 H) 3.58 - 3.68 (m, 2 H) 3.76 - 3.85 (m, 2 H) 3.95 (s, 3 H) 4.30 - 4.37 (m, 1 H) 5.62 (dd, 8.11, 6.59 Hz, 1 H) 7.60 (dd, J = 8.49, 1.39 Hz, 1 H) 7.80 (d, J = 8.62 Hz, 1 H) 8.00 - 8.04 (m, 1 H) 8.67 (d, J = 0.89 Hz, 1 H) 9.05 - 9.09 (m, 2 H)

Example 1-1: N-[(1,4-dioxan-2-yl)[1-methyl-5-(trifluoromethyl)-1H-1,3-benzodiazol-2-yl]methyl]-5-methylpyrazine-2-carboxamide

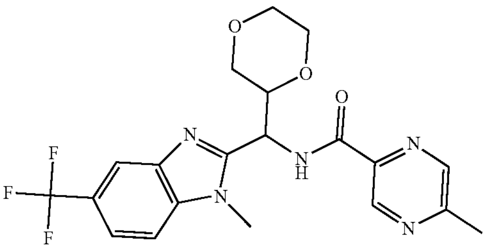 [SMILES: Cc1cnc(C(=O)NC(c2nc3cc(C(F)(F)F)ccc3n2C)C2COCCO2)cn1]

HPLC-MS; Method: Z018_S04; $R_t$ [min]: 0.94 — MS: 436 $(M + H)^+$

Chiral SFC Rt Method: I_C2_20_MEOH_NH3_002 — Rt [min]: 0.99

$^1H$ NMR (400 MHz, DMSO-$d_6$) δ ppm 2.55 - 2.63 (m, 3 H) 3.45 - 3.58 (m, 3 H) 3.58 - 3.76 (m, 2 H) 3.93 (s, 3 H) 4.02 (dd, J = 11.34, 2.34 Hz, 1 H) 4.26 (td, J = 9.28, 2.47 Hz, 1 H) 5.48 (t, J = 8.74 Hz, 1 H) 7.58 (dd, J = 8.62, 1.39 Hz, 1 H) 7.79 (d, J = 8.49 Hz, 1 H) 8.01 (s, 1 H) 8.66 (d, J = 1.01 Hz, 1 H) 9.02 (d, J = 1.39 Hz, 1 H) 9.32 (d, J = 8.49 Hz, 1 H)

Example 2

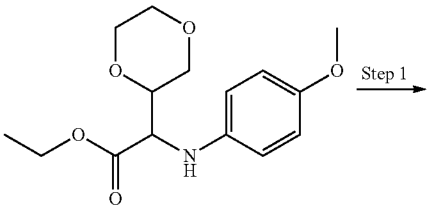

Int-3b

-continued

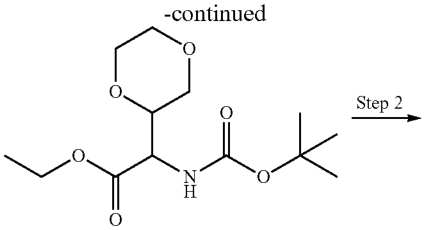

Int-2a

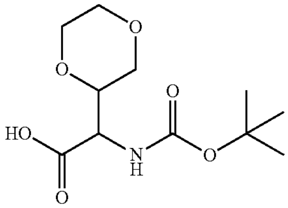

Int-2b

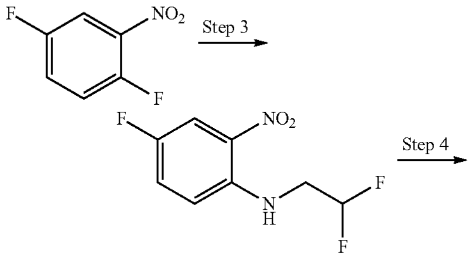

Int-2c

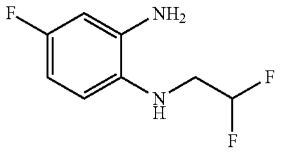

Int-2d

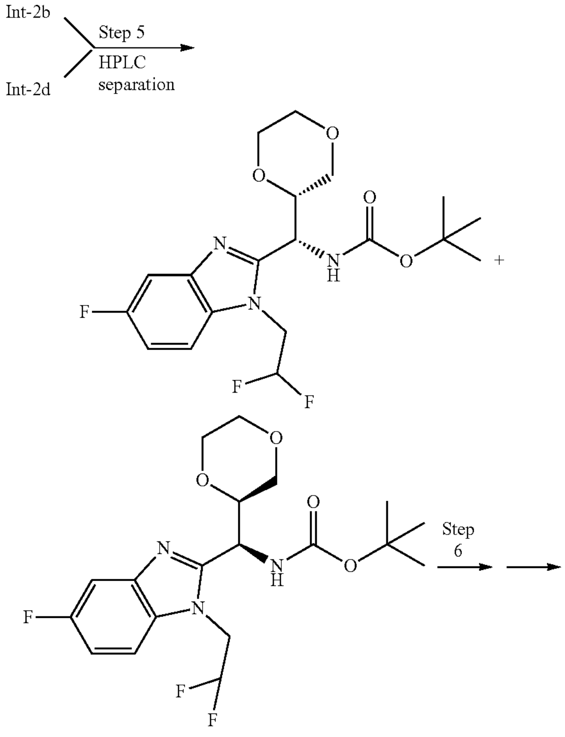

Int-2e

-continued

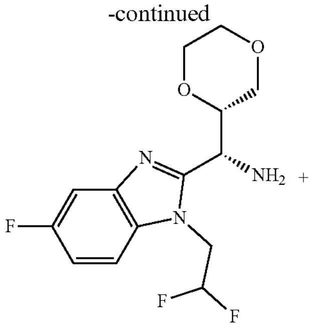

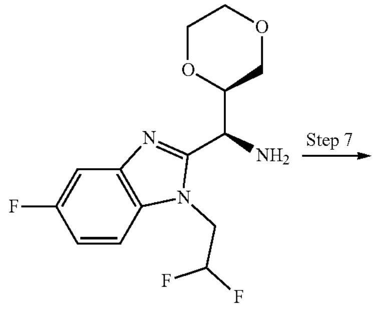

Int-2f

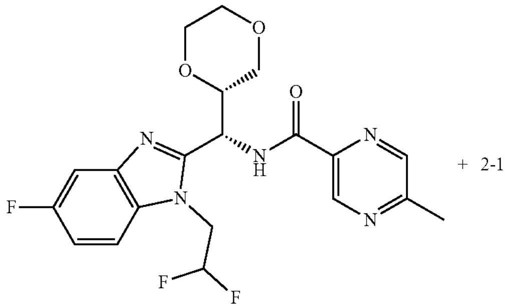

Example 2

Step 1:

To Int-3b (1.30 g, 4.4 mmol) in 30 mL ACN and 10 mL water is added cer(IV)-ammonium nitrate (3.62 g, 6.6 mmol) and the mixture stirred at ambient temperature for 3 h. Then, the mixture is concentrated i. vac., the residue taken up with water and extracted with EtOAc. The combined organic layers are dried over $Na_2SO_4$ and concentrated i. vac. The residue is taken up in 3 mL THF and 10 mL TEA, $Boc_2O$ (3.48 g, 6.4 mmol) is added and the mixture stirred at ambient temperature for 3 h. Afterwards, the mixture is concentrated i. vac.

Yield: 0.80 g (2.8 mmol; 63%) Int-2a

MS ($ESI^+$): $(M+H)^+$ 290

Step 2:

LiOH (0.10 g, 4.2 mmol) is added to Int-2a (0.80 g, 2.8 mmol) in 10 mL MeOH and 3 mL water and the mixture stirred at ambient temperature for 3 h. Then the mixture is concentrated i. vac. and purified by prep. HPLC.

Yield: 0.60 g (2.3 mmol, 82%) Int-2b as mixture of stereoisomers

MS ($ESI^+$): $(M+H)^+$ 262

Step 3:

A mixture of 1,4-difluoro-2-nitro-benzene (100 g; 0.63 mol) and 2,2-difluoroethylamine (266 mL; 3.8 mol) in 800 mL ACN with $K_2CO_3$ (400 g; 1.3 mol) is stirred at 80° C. for 2d. The mixture is filtered, and the filtrate is concentrated i. vac. The residue is used without further purification.

$R_f$: 0.4 (PE/EtOAc 85:15)

Yield: 105 g (0.48 mol; 76%) Int-2c

MS (ESI$^+$): $(M+H)^+$ 221; HPLC: RT=1.00 min, Method: Z018_S04

Step 4:

A mixture of Int-2c (50 g, 0.23 mol) with 10 g Raney-nickel in 500 mL MeOH is hydrogenated at ambient temperature at 50 psi (hydrogen gas) for 4 h. Afterwards, the mixture is filtered, washed with EtOAc and concentrated i. vac. The residue is used without further purification.

$R_f$: 0.4 (PE/EtOAc 85:15)

Yield: 45 g (0.22 mol; 98%) Int-2d

MS (ESI$^+$): $(M+H)^+$ 191; HPLC: RT=0.71 min, Method: Z018_S04

Step 5:

To a mixture of int-2d (280 mg, 1.4 mmol), Int-2b (377 mg, 1.4 mmol) and NMM (0.95 mL, 8.7 mmol) in 3 mL DCM is added PPA (50% in EtOAc; 1.3 mL, 2.2 mmol) at 0° C. After 2 h stirring at 0° C., the mixture is concentrated i. vac. Then 2.1 g acetic acid is added and the mixture stirred at 50° C. for 8d. The mixture is concentrated i. vac. The mixture contains four stereoisomers, which can be separated into two pairs of enantiomers via prep. HPLC (C-18 Sunfire 10 μm, eluent gradient (water+0.15% TFA):ACN 64:36→44:56). The product containing fractions are combined and freeze-dried. Only one pair of enantiomers (Int-2e) is used in step 6 which is depicted in the reaction scheme.

Stereoisomer pair 1: Int-2e as a mixture of enantiomers: Yield: 119 mg (0.29 mmol; 20%) MS (ESI$^+$): $(M+H)^+$ 416; HPLC: RT=0.98 min, Method: Z018_S04

Stereoisomer pair 2 as a mixture of enantiomers: Yield: 104 mg (0.25 mmol; 17%) MS (ESI$^+$): $(M+H)^+$ 416; HPLC: RT=0.97 min, Method: Z018_S04

Step 6:

Int-2e (119 mg, 0.29 mmol) is stirred at ambient temperature for 2 h in HCl in dioxane (4N; 3.0 mL, 12 mmol). The mixture is concentrated i. vac.

Yield: 111 mg (0.29 mmol; quant.) Int-2f as mixture of enantiomers

MS (ESI$^+$): $(M+H)^+$ 316

Step 7:

A mixture of Int-2f (111 mg, 0.29 mmol), 5-methyl-pyrazine-2-carboxylic acid (39 mg, 0.29 mmol) and NMM (189 μL, 1.7 mmol) in 3.5 mL DCM is stirred at 0° C., PPA (50% in EtOAc; 0.3 mL, 0.5 mmol) is added and the mixtures stirred for 1 h at 0° C. The mixture is concentrated i. vac., taken up in ACN, filtered and the filtrate purified by prep. HPLC (C-18 X-Bridge 10 μm, eluent gradient (water+0.15% $NH_3$):ACN 71:29→51:49). The product containing fractions are combined and freeze-dried. Afterwards chiral SFC is performed to get the desired enantiomers (example 2 and 2-1).

Yield: 28 mg example 2 and 25 mg example 2-1

Example 2: N-[(R)-[1-(2,2-difluoroethyl)-5-fluoro-1H-1,3-benzodiazol-2-yl][(2S)-1,4-dioxan-2-yl]methyl]-5-methylpyrazine-2-carboxamide

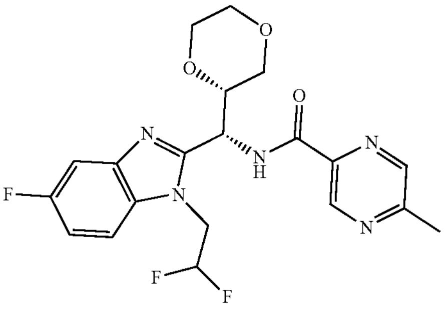 [SMILES: Cc1cnc(C(=O)N[C@H](c2nc3cc(F)ccc3n2CC(F)F)[C@H]2COCCO2)cn1]

HPLC-MS; Method: Z011_S03; $R_t$ [min]: 0.90 MS: 436 $(M + H)^+$
Chiral SFC Rt Method: I_IG_25_MEOH_NH3_001 Rt [min]: 4.14
$^1$H NMR (400 MHz, DMSO-$d_6$) δ ppm 2.60 (s, 3 H) 3.37 - 3.49 (m, 1 H) 3.57 - 3.68 (m, 2 H) 3.70 - 3.77 (m, 1 H) 3.78 - 3.85 (m, 1 H) 4.36 - 4.43 (m, 1 H) 4.89 - 5.14 (m, 2 H) 5.54 (t, J = 7.73 Hz, 1 H) 6.47 (m, 1 H) 7.18 (m, 1 H) 7.50 (dd, J = 9.57, 2.47 Hz, 1 H) 7.65 (dd, J = 8.93, 4.75 Hz, 1 H) 8.65 (d, J = 1.01 Hz, 1 H) 9.05 (d, J = 1.39 Hz, 1 H) 9.10 (d, J = 8.24 Hz, 1 H)

Example 2-1: N-[(S)-[1-(2,2-difluoroethyl)-6-(trifluoromethyl)-1H-1,3-benzodiazol-2-yl][(2R)-1,4-dioxan-2-yl]methyl]-5-methylpyrazine-2-carboxamide:

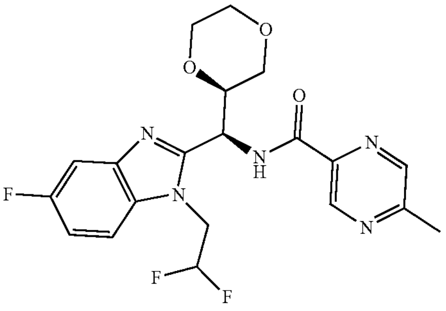 [SMILES: Cc1cnc(C(=O)N[C@@H](c2nc3cc(F)ccc3n2CC(F)F)[C@@H]2COCCO2)cn1]

HPLC-MS; Method: Z011_S03; $R_t$ [min]: 0.90 MS: 436 $(M + H)^+$
Chiral SFC Rt Method: I_IG_25_MEOH_NH3_001 Rt [min]: 2.5
$^1$H NMR (400 MHz, DMSO-$d_6$) δ ppm 2.58 - 2.61 (m, 3 H) 3.23 - 3.28 (m, 1 H) 3.38 - 3.55 (m, 1 H) 3.55 - 3.69 (m, 2 H) 3.73 (dd, J = 11.41, 2.41 Hz, 1 H) 3.81 (br d, J = 11.28 Hz, 1 H) 4.37 - 4.43 (m, 1 H) 4.89 - 5.13 (m, 2 H) 5.54 (t, J = 7.73 Hz, 1 H) 6.28 - 6.65 (m, 1 H) 7.18 (td, J = 9.31, 2.41 Hz, 1 H) 7.51 (dd, J = 9.57, 2.47 Hz, 1 H) 7.65 (dd, J = 8.93, 4.75 Hz, 1 H) 8.65 (d, J = 1.14 Hz, 1 H) 9.05 (d, J = 1.39 Hz, 1 H) 9.11 (d, J = 8.24 Hz, 1 H)

Example 3

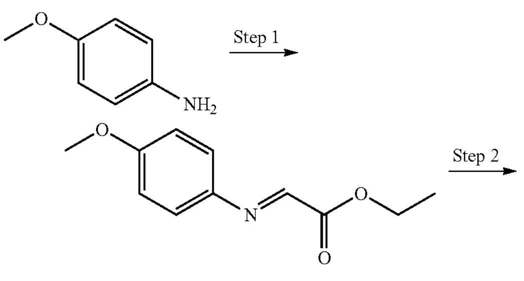

Int-3a

-continued

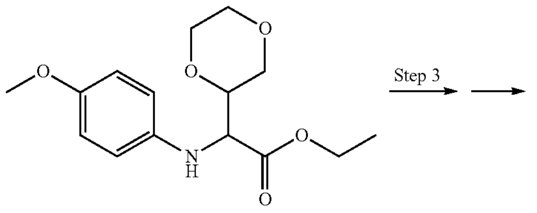

Int-3b

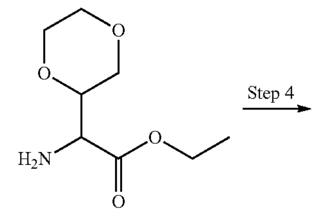

Int-3c

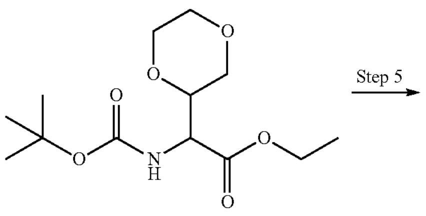

Int-3d

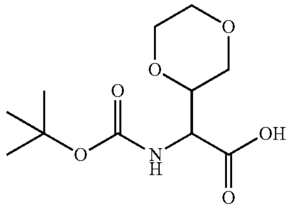

Int-3e

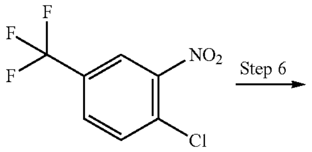

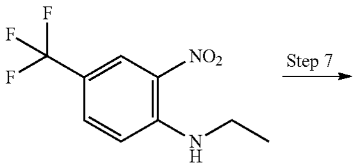

Int-3f

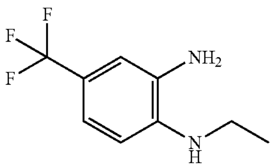

Int-3g

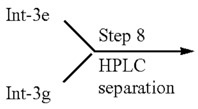

-continued

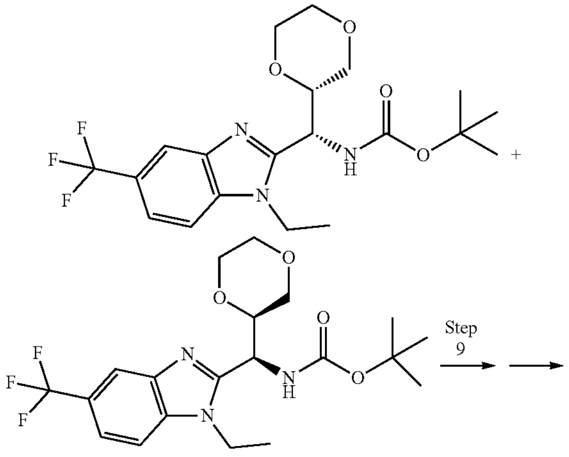

Int-3h

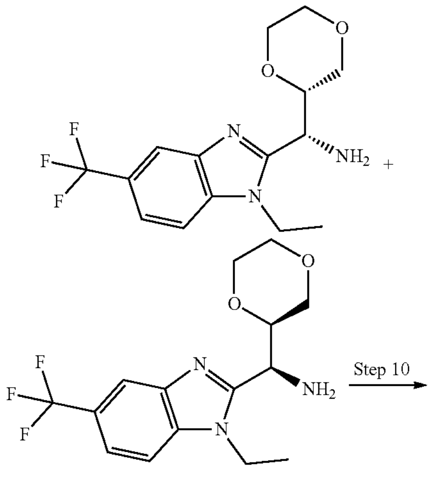

Int-3i

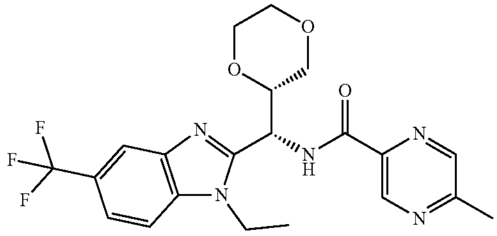

Example 3

Step 1:

A mixture of 4-methoxy-aniline (10 g, 81 mmol), ethyl glyoxylate polymer form (47% in toluene, 17 mL, 81 mmol) and $MgSO_4$ (24 g, 203 mmol) in 125 mL DCM is stirred at 40° C. for 3 h. The mixture is filtered and the filtrate is evaporated at 25° C. The residue is used without further purification. Yield: 20.8 g (~80% content; 81 mol; quant.) Int-3a MS ($ESI^+$): $(M+H)^+$ 208; HPLC: RT=0.90 min, Method: Z011_S03

Step 2:

Int-3a (21 g 80% content, 81 mmol) in 150 mL dioxane (without stabilizer) is de-gassed and kept under nitrogen. Copper(I1)chloride (0.54 g, 4 mmol) and tert.-butyl hydroperoxide (5.5M in decane; 17.5 mL, 96 mmol) are added and the mixture stirred at 50° C. for 16 h. The mixture is concentrated i. vac. and purified by consecutive column chromatographies (silica gel, PE/EtOAc gradient 9:1→4:1, then 7:3, then 4:1, each time product containing fractions combined and concentrated i. vac. before next purification).

Yield: 6.4 g (22 mmol; 27%) Int-3b as mixture of stereoisomers

MS (ESI$^+$): $(M+H)^+$ 296; HPLC: RT=0.90 min, Method: Z011_S03

Step 3

Int-3b (300 mg, 1.02 mmol) together with ammonium cerium(IV) nitrate (835 mg, 1.6 mmol) in 10 mL ACN with 3 mL water is stirred at ambient temperature for 3 h. Afterwards, the mixture is filtered and concentrated i. vac.

Yield: 300 mg (purity: ~33%; 0.53 mmol; 52%) Int-3c as mixture of stereoisomers

MS (ESI$^+$): $(M+H)^+$ 190; TLC: Rf=0.5 (Eluent: DCM: MeOH 95:5)

Step 4:

Boc-anhydryde (5.2 g; 24 mmol) is added to a mixture of Int-3c (3.0 g; 16 mmol) with TEA (8.0 g; 79 mmol) in 15 mL THF and the mixture stirred at ambient temperature for 18 h followed by concentration i. vac. and purification via silica gel column chromatography (eluent-gradient: hexane: EtOAc 100:0→60:40).

Yield: 1.0 g (purity: ~65%; 2.2 mmol; 9%) Int-3d as mixture of stereoisomers

MS (ESI$^+$): $(M+H)^+$ 234; TLC: Rf=0.5 (Eluent: hexane: EtOAc 7:3)

Step 5:

LiOH (100 mg; 4.2 mmol) is added to Int-3d (0.8 g, 2.8 mmol) in 10 mL MeOH with 3 mL water, and the mixture stirred at ambient temperature for 3 h, concentrated i. vac. and purified by prep.

HPLC.

Yield: 0.5 g (1.9 mmol; 68%) Int-3e as mixture of stereoisomers

MS (ESI$^+$): $(M+H)^+$ 262; TLC: Rf=0.5 (Eluent: DCM: MeOH 95:5)

Step 6:

To 1-fluoro-2-nitro-4-trifluoromethyl-benzene (2.2 mL; 15.7 mmol) in 100 mL DCM is added ethylamine (2M in THF; 15.7 mL, 31.4 mmol) and the mixture stirred for 20 h at ambient temperature. 100 mL DCM are added and the mixture extracted with 100 mL water. The organic layer is collected, dried over $Na_2SO_4$, filtered and concentrated i. vac.

Yield: 3.30 g (14.1 mmol; 90%) Int-3f

MS (ESI$^+$): $(M+H)^+$ 235; HPLC: RT=1.10 min, Method: Z017_S04

Step 7:

Int-3f (200 mg, 0.85 mmol) is mixed with palladium on charcoal (10%, 50 mg) in 20 mL MeOH and hydrogenated for 3.5 h at 50 psi hydrogen pressure. Then the mixture is filtered and concentrated i. vac.

Yield: 170 mg (0.83 mol; 97%) Int-3 g

MS (ESI$^+$): $(M+H)^+$ 205; HPLC: RT=0.86 min, Method: Z018_S04

Step 8:

Int-3e (210 mg, 0.80 mmol), Int-3 g (170 mg, 0.83 mmol) and 3500_ NMM in 5 mL DCM are stirred at ambient temperature and PPA (50% in EtOAc; 600 μL, 1.0 mmol) is added. After stirring for 16 h at ambient temperature, water is added and the mixture stirred at ambient temperature for 20 min. Then 5 mL AcOH is added and the mixture stirred at 50° C. for 3 h, at ambient temperature for 16 h and at 80° C. for 2 h. The mixture contains four stereoisomers, which can be separated into two pairs of enantiomers by HPLC (C-18 Sunfire at 50° C., eluent gradient (water+0.15% TFA):

ACN 58:42→38:62). The product containing fractions are combined and freeze-dried. Only one pair of enantiomers (Int-60 h) is used in step 9 which is depicted in the reaction scheme.

Stereoisomer Pair 1: Yield: 70 mg (0.13 mmol; 16%) Int-3 h as mixture of enantiomers MS (ESI$^+$): $(M+H)^+$ 430; HPLC: RT=1.03 min, Method: Z018_504

Stereoisomer Pair 2: Yield: 120 mg as a mixture of enantiomers

MS (ESI$^+$): $(M+H)^+$ 430; HPLC: RT=1.04 min, Method: Z018_S04

Step 9:

Int-3 h (70 mg, 0.13 mmol) is stirred in 4 mL hydrochloric acid (4M in dioxane) at ambient temperature for 1 h. The mixture is concentrated i. vac.

Yield: 52 mg (0.13 mmol; quant.) Int-3 i as mixture of enantiomers

MS (ESI$^+$): $(M+H)^+$ 330; HPLC: RT=0.77 min, Method: Z018_S04

Step 10:

A mixture from Int-3i (52 mg, 0.13 mmol), 5-methyl-pyrazine-2-carboxylic acid (22 mg, 0.16 mmol), TBTU (44 mg, 0.14 mmol) and TEA (1000_, 0.72 mmol) in 4.0 mL DMF is stirred at ambient temperature for 15 min. Water is added and the mixture is purified by prep. HPLC (C-18 X-Bridge at 50° C., eluent gradient (water+0.15% $NH_3$): ACN 61:39→41:59). The product containing fractions are combined and freeze-dried. Afterwards chiral SFC is performed to get the desired stereoisomer.

Yield: 15 mg (0.033 mol; 36%) example 3

Example 3: N-[(R)-[(2S)-1,4-dioxan-2-yl][1-ethyl-5-(trifluoromethyl)-1H-1,3-benzodiazol-2-yl]methyl]-5-methylpyrazine-2-carboxamide

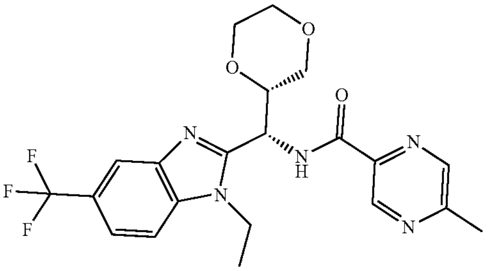 [SMILES: CCn1c([C@@H](NC(=O)c2cnc(C)cn2)[C@H]2COCCO2)nc2cc(C(F)(F)F)ccc21]

HPLC-MS; Method: Z018_S04; $R_t$ [min]: 0.99 MS: 450 $(M+H)^+$
Chiral SFC Rt Method: I_C2_15_MEOH_NH3_002 Rt [min]: 1.50
$^1H$ NMR (400 MHz, DMSO-$d_6$) δ ppm 1.28 - 1.37 (m, 3 H) 2.60 (s, 3 H) 3.31 - 3.39 (m, 1 H) 3.42 - 3.53 (m, 1 H) 3.58 - 3.68 (m, 2 H) 3.77 - 3.86 (m, 2 H) 3.95 (s, 3 H) 4.30 - 4.37 (m, 1 H) 4.38 - 4.57 (m, 2 H) 5.64 (dd, J = 8.30, 7.29 Hz, 1 H) 7.59 (dd, J = 8.62, 1.39 Hz, 1 H) 7.83 (d, J = 8.49 Hz, 1 H) 8.03 (s, 1 H) 8.66 (d, J = 1.01 Hz, 1 H) 9.06 (d, J = 1.39 Hz, 1 H) 9.10 (d, J = 8.36 Hz, 1 H)

Example 4 and Example 5

In analogy to example 1 (see below), starting from 4-chloro-1-fluoro-2-nitrobenzene and except step 7 the following compounds are obtained:

Example 1
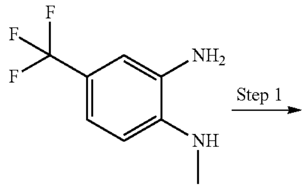
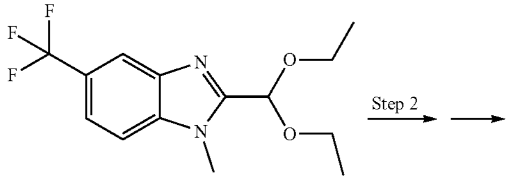
Int-1a
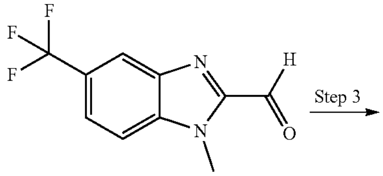
Int-1b
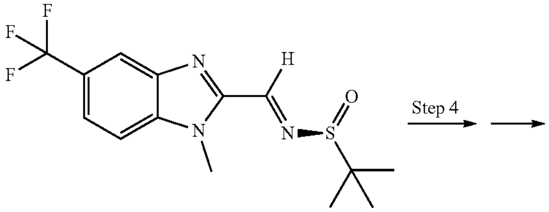
Int-1c
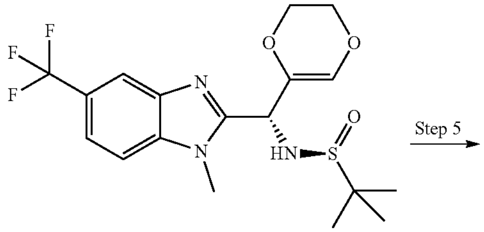
Int-1d
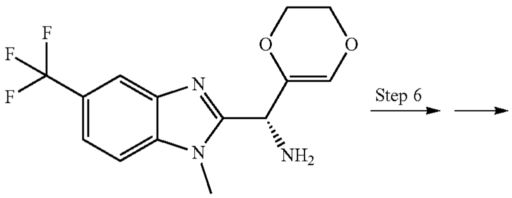
Int-1e
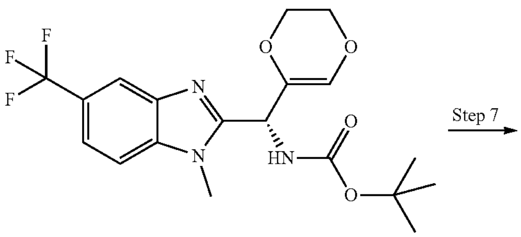
Int-1f
-continued
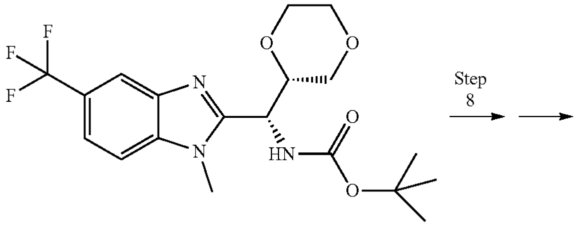
Int-1g
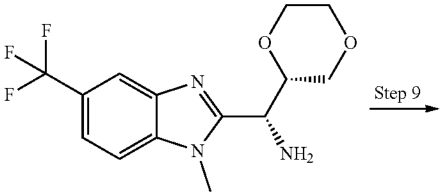
Int-1h
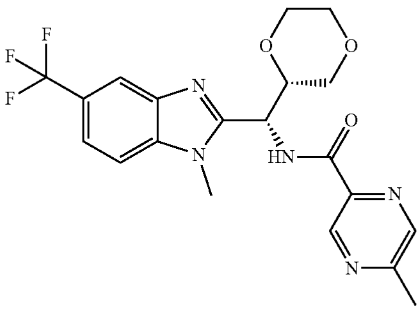
Example 1, 1-1
Example 4 and Example 5
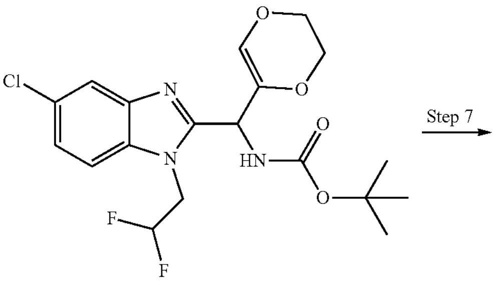
Int-4f
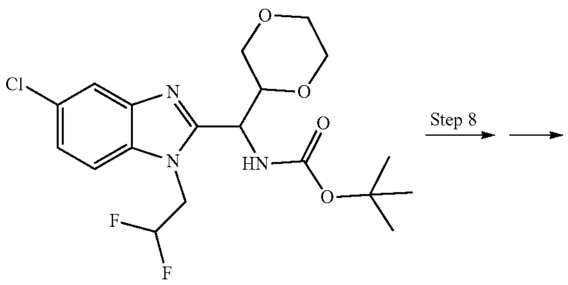
Int-4g -continued

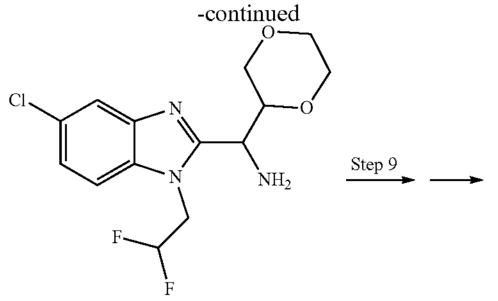

Int-4h

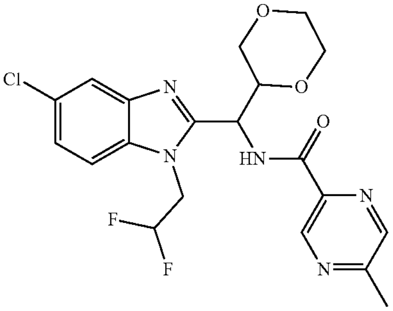

+ Example 5

Example 4

Step 7:

A mixture of Int-4f (2.9 g, 6.75 mmol) and Wilkinsons catalyst (950 mg, 1.03 mmol) in ethanol (145 ml) is hydrogenated under a hydrogen atmosphere at 40 psi and 40° C. for 22 h. The mixture is filtered and concentrated in vacuo. The residue is dissolved in THF/MeOH and purified by column chromatography (XBridge C18,10 μm, eluent gradient: ($H_2O$+0,1% $NH_4OH$): 58:42→38:62 I). The fractions containing product are combined and concentrated i.vac. The product is isolated as a mixture of stereoisomers and used as such in the following step.

Yield: 2.05 g (4.74 mmol; 70,4%) Int-4 g

MS (ESI$^+$): (M+H)+432, HPLC: RT=1.03 min, Method: Z011_503

Chiral SFC Rt stereoisomer 1: 0.66 min (Method: I_AC_10_IPA_NH3_002)

Chiral SFC Rt stereoisomer 2: 0.86 min (Method: I_AC_10_IPA_NH3_002)

Step 8:

Synthesized analogous to Example 1 step 8 from Int-4 g giving the title compounds as a mixture of stereoisomers which are used as such in the next step Yield: 1,18 g (3.56 mmol; 76,8%) Int-4 h MS (ESI$^+$): $(M+H)^+$ 332; HPLC: RT=0.84 min, Method: Z011_S03

Chiral SFC Rt diastereoisomer 1: 1.23 min (Method: I_IG_20_MEOH_NH3_002)

Chiral SFC Rt diastereoisomer 2: 1.56 min (Method: I_IG_20_MEOH_NH3_002)

Step 9:

Synthesized in analogy to Example 1 step 9 from Int-4 h giving example 4 and example 5 as a mixture of stereoisomers which are separated by chiral SFC.

Yield: 1,18 g (3.56 mmol; 76,8%) example 4 and 5

MS (ESI$^+$): $(M+H)^+$ 332; HPLC: RT=0.84 min, Method: Z011_S03

Example 4: N-{[5-chloro-1-(2,2-difluoroethyl)-1H-1,3-benzodiazol-2-yl](1,4-dioxan-2-yl)methyl}-5-methylpyrazine-2-carboxamide

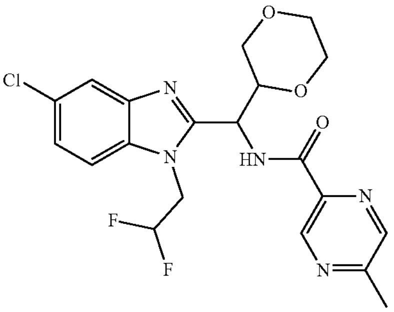 [SMILES: Cc1cnc(C(=O)NC(c2nc3cc(Cl)ccc3n2CC(F)F)C2COCCO2)cn1]

HPLC-MS; Method: Z011_S03; $R_t$ [min]: 0.96 MS: 452 $(M + H)^+$
Chiral SFC Rt Method: I_C2_20_MeOH_NH3_002 Rt [min]: 1,42
$^1$H NMR (400 MHz, DMSO-$d_6$) δ ppm-2.58 – 2.61 (m, 3 H) –3.17 – 3.28 (m, 1 H)–3.41 – 3.58 (m, 1 H) –3.58 – 3.70 (m, 2 H) 3.73 (dd, J = 11.41, 2.28 Hz, 1 H) 3.81 (br d, J = 11.41 Hz, 1 H) –4.37 – 4.43 (m, 1 H) –4.89 – 5.15 (m, 2 H) –5.52 – 6.35 (m, 1 H) –6.45 – 6.63 (m, 1 H) 7.34 (dd, J = 8.68, 1.96 Hz, 1 H) 7.67 (d, J = 8.74 Hz, 1 H) 7.76 (d, J = 1.90 Hz, 1 H) 8.65 (d, J = 1.01 Hz, 1 H) 9.05 (d, J = 1.39 Hz, 1 H) 9.11 (d, J = 8.24 Hz, 1 H)

Example 5: N-{[5-chloro-1-(2,2-difluoroethyl)-1H-1,3-benzodiazol-2-yl](1,4-dioxan-2-yl)methyl}-5-methylpyrazine-2-carboxamide

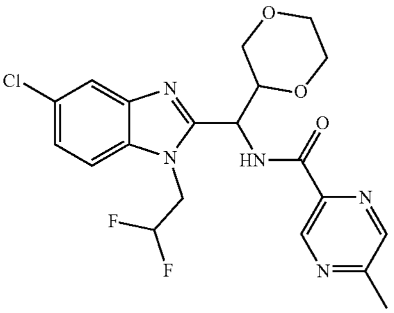 [SMILES: Cc1cnc(C(=O)NC(c2nc3cc(Cl)ccc3n2CC(F)F)C2COCCO2)cn1]

HPLC-MS; Method: Z011_S03; $R_t$ [min]: 0.96 MS: 452 $(M + H)^+$
Chiral SFC Rt Method: I_C2_20_MeOH_NH3_002 Rt [min]: 0,99
$^1$H NMR (400 MHz, DMSO-$d_6$) δ ppm 2.59 (s, 3 H) –3.43 – 3.58 (m, 3 H) –3.58 – 3.70 (m, 2 H) 3.98 (dd, J = 11.22, 2.22 Hz, 1 H) 4.22 (td, J = 9.47, 2.34 Hz, 1 H) –4.85 – 5.04 (m, 2 H) 5.48 (t, J = 8.87 Hz, 1 H) –6.30 – 6.60 (m, 1 H) 7.32 (dd, J = 8.62, 2.03 Hz, 1 H) 7.65 (d, J = 8.74 Hz, 1 H) 7.75 (d, J = 1.90 Hz, 1 H) 8.65 (s, 1 H) 9.03 (d, J = 1.27 Hz, 1 H) 9.28 (d, J = 8.62 Hz, 1 H)

In analogy to example 1, starting from 2-fluoro-1-nitro-4-(trifluoromethyl)benzene, the following compound is obtained. The product is a mixture of two stereoisomers. One stereoisomer is isolated: example 6

Example 6: N-[-[1-(2,2-difluoroethyl)-6--(trifluoromethyl)1H-1,3-benzodiazol-2-yl][-1,4-dioxan-2-yl]methyl]-5-methylpyrazine-2-carboxamide -continued

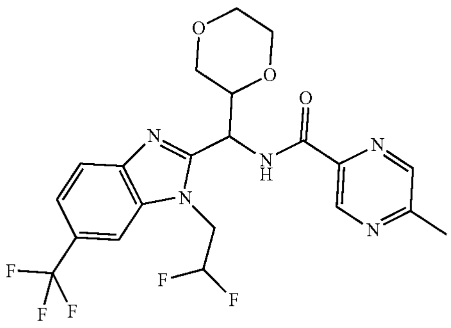 [SMILES: Cc1cnc(C(=O)NC(c2nc3ccc(C(F)(F)F)cc3n2CC(F)F)C2COCCO2)cn1]

HPLC-MS; Method: Z011_S03; $R_t$ [min]: 0.99 MS: 486 $(M + H)^+$
Chiral SFC Rt Method: I_SZ_10_MeOH_NH3_003 Rt [min]: 1,85
$^1$H NMR (400 MHz, DMSO-$d_6$) δ ppm −2.58 − 2.62 (m, 3 H) 3.31 (br s, 1 H) −3.37 − 3.54 (m, 1 H) −3.54 − 3.70 (m, 2 H) −3.70 − 3.84 (m, 2 H) −4.39 − 4.46 (m, 1 H) −5.02 − 5.27 (m, 2 H) −5.57 − 5.75 (m, 1 H) −6.36 − 6.67 (m, 1 H) 7.58 (dd, J = 8.62, 1.39 Hz, 1 H) 7.89 (d, J = 8.49 Hz, 1 H) 8.13 (s, 1 H) 8.66 (d, J = 1.01 Hz, 1 H) 9.06 (d, J = 1.39 Hz, 1 H) 9.15 (d, J = 8.24 Hz, 1 H)

In analogy to example 1, starting from 2-fluoro-1-nitro-4-(trifluoromethyl)benzene the following compounds are obtained. The product is a mixture of two stereoisomers which are separated by chiral SFC: examples 7, 7-1, Example 7: N-[(1,4-dioxan-2-yl)[1-methyl-6-(trifluoromethyl)-1H-1,3-benzodiazol-2-yl]methyl]-5-methylpyrazine-2-carboxamide

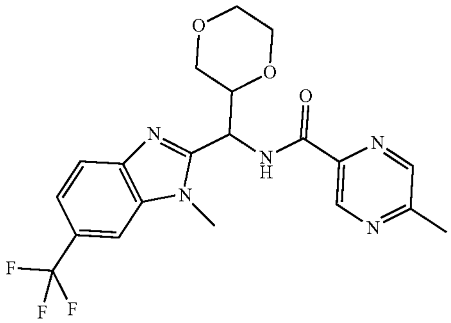 [SMILES: Cc1cnc(C(=O)NC(c2nc3ccc(C(F)(F)F)cc3n2C)C2COCCO2)cn1]

HPLC-MS; Method: Z011_S03; $R_t$ [min]: 0.96 MS: 436 $(M + H)^+$
Chiral SFC Rt Method: I_IG_35_IPA_NH3_003 Rt [min]: 2,9
$^1$H NMR (400 MHz, DMSO-$d_6$) δ ppm 2.61 (s, 3 H) 3.34 (dd, J = 11.47, 9.19 Hz, 1 H) −3.40 − 3.53 (m, 1 H) −3.53 − 3.73 (m, 2 H) −3.73 − 3.91 (m, 2 H) 3.98 (s, 3 H) 4.33 (ddd, J = 9.03, 6.56, 2.53 Hz, 1 H) 5.63 (dd, J = 8.11, 6.59 Hz, 1 H) 7.53 (dd, J = 8.49, 1.52 Hz, 1 H) 7.83 (d, J = 8.49 Hz, 1 H) 8.05 (s, 1 H) 8.67 (d, J = 1.01 Hz, 1 H) 9.06 (s, 1 H) 9.07 (d, J = 7.04 Hz, 1 H).

Example 7-1: N-[(1,4-dioxan-2-yl)[1-methyl-6-(trifluoromethyl)-1H-1,3-benzodiazol-2-yl]methyl]-5-methylpyrazine-2-carboxamide -continued

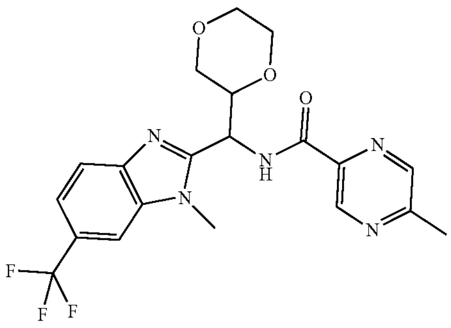 [SMILES: Cc1cnc(C(=O)NC(c2nc3ccc(C(F)(F)F)cc3n2C)C2COCCO2)cn1]

HPLC-MS; Method: Z011_S03; $R_t$ [min]: 0.96 MS: 436 $(M + H)^+$
Chiral SFC Rt Method: I_IG_35_IPA_NH3_003 Rt [min]: 4,44
$^1$H NMR (400 MHz, DMSO-$d_6$) δ ppm 2.59 (s, 3 H) −3.45 − 3.58 (m, 3 H) −3.58 − 3.80 (m, 2 H) 3.95 (s, 3 H) −3.98 − 4.17 (m, 1 H) 4.26 (td, J = 9.28, 2.47 Hz, 1 H) 5.49 (t, J = 8.74 Hz, 1 H) 7.52 (dd, J = 8.49, 1.52 Hz, 1 H) 7.83 (d, J = 8.49 Hz, 1 H) 8.04 (s, 1 H) 8.66 (d, J = 1.01 Hz, 1 H) 9.02 (d, J = 1.27 Hz, 1 H) 9.31 (d, J = 8.49 Hz, 1 H).

In analogy to example 1, starting from 2,4-difluoro-1-nitrobenzene, the following compounds are obtained. The product is a mixture of two stereoisomers which are separated by chiral SFC: examples 8, 8-1

Example 8: N-[(R)-[1-(2,2-difluoroethyl)-6-fluoro-1H-1,3-benzodiazol-2-yl][(2S)-1,4-dioxan-2-yl]methyl]-5-methylpyrazine-2-carboxamide

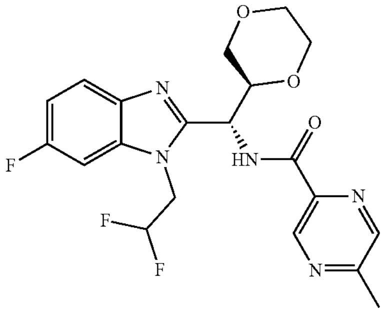 [SMILES: Cc1cnc(C(=O)N[C@H](c2nc3ccc(F)cc3n2CC(F)F)[C@H]2COCCO2)cn1]

HPLC-MS; Method: Z011_S03; $R_t$ [min]: 0.90 MS: 436 $(M + H)^+$
Chiral SFC Rt Method: I_SZ_10_MEOH_NH3_003 Rt [min]: 2,75
$^1$H NMR (400 MHz, DMSO-$d_6$) δ ppm 2.60 (s, 3 H) −3.24 − 3.28 (m, 1 H) −3.41 − 3.55 (m, 1 H) −3.55 − 3.68 (m, 2 H) −3.68 − 3.84 (m, 2 H) −4.36 − 4.43 (m, 1 H) −4.85 − 5.12 (m, 2 H) 5.54 (t, J = 7.79 Hz, 1 H) −6.32 − 6.62 (m, 1 H) 7.11 (ddd, J-9.79, 8.90, 2.47 Hz, 1 H) 7.54 (dd, J = 9.38, 2.28 Hz, 1 H) 7.69 (dd, J = 8.87, 4.94 Hz, 1 H) 8.65 (d, J = 1.01 Hz, 1 H) 9.06 (d, J = 1.27 Hz, 1 H) 9.09 (d, J = 8.24 Hz, 1 H).

Example 8-1: N-{[1-(2,2-difluoroethyl)-6-fluoro-1H-1,3-benzodiazol-2-yl](1,4-dioxan-2-yl)methyl}-5-methylpyrazine-2-carboxamide -continued

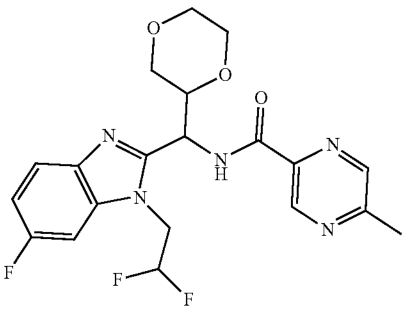 [SMILES: Cc1cnc(C(=O)NC(c2nc3ccc(F)cc3n2CC(F)F)C2COCCO2)cn1]

| | |
|---|---|
| HPLC-MS; Method: Z011_S03; $R_t$ [min]: 0.90 | MS: 436 $(M + H)^+$ |
| Chiral SFC Rt Method: I_SZ_10_MEOH_NH3_003 | Rt [min]: 2,01 |
| $^1$H NMR (400 MHz, DMSO-$d_6$) δ ppm 2.59 (s, 3 H) −3.36 − 3.57 (m, 3 H) −3.57 − 3.91 (m, 2 H) 3.98 (dd, J = 11.34, 2.22 Hz, 1 H) 4.21 (td, J = 9.47, 2.34 Hz, 1 H) −4.82 − 4.99 (m, 2 H) 5.47 (t, J = 8.87 Hz, 1 H) −6.30 − 6.69 (m, 1 H) 7.10 (t, J = 9.21 Hz, 1 H) 7.53 (dd, J = 9.38, 2.28 Hz, 1 H) 7.68 (dd, J = 8.81, 4.88 Hz, 1 H) 8.65 (d, J = 0.89 Hz, 1 H) 9.03 (d, J = 1.27 Hz, 1 H) 9.24 (d, J = 8.62 Hz, 1 H). | |

In analogy to example 1,starting from 1,2,4-trifluoro-5-nitrobenzene, the following compounds are obtained. The product is a mixture of two stereoisomers which are separated by chiral SFC: examples 9, 9-1

Example 9: N-{[1-(2,2-difluoroethyl)-5,6-difluoro-1H-1,3-benzodiazol-2-yl](1,4-dioxan-2-yl)methyl}-5-methylpyrazine-2-carboxamide

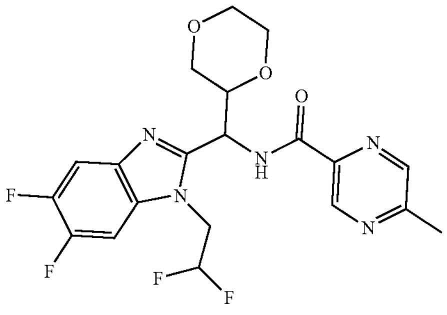 [SMILES: Cc1cnc(C(=O)NC(c2nc3cc(F)c(F)cc3n2CC(F)F)C2COCCO2)cn1]

| | |
|---|---|
| HPLC-MS; Method: Z011_S03; $R_t$ [min]: 0.83 | MS: 454 $(M + H)^+$ |
| Chiral SFC Rt Method: I_SZ_15_MEOH_NH3_003 | Rt [min]: 1,85 |
| $^1$H NMR (400 MHz, DMSO-$d_6$) δ ppm 2.60 (s, 3 H) −3.24 − 3.30 (m, 1 H) −3.41 − 3.55 (m, 1 H) −3.55 − 3.69 (m, 2 H) 3.73 (dd, J = 11.41, 2.41 Hz, 1 H) 3.81 (br d, J = 11.53 Hz, 1 H) −4.36 − 4.42 (m, 1 H) −4.88 − 5.13 (m, 2 H) 5.53 (t, J = 7.73 Hz, 1 H) −6.22 − 6.63 (m, 1 H) −7.75 − 7.85 (m, 2 H) 8.65 (d, J = 1.01 Hz, 1 H) 9.05 (d, J = 1.39 Hz, 1 H) 9.11 (d, J = 8.24 Hz, 1 H). | |

Example 9-1:N-[(R)-[1-(2,2-difluoroethyl)-5,6-difluoro-1H-1,3-benzodiazol-2-yl][(2S)-1,4-dioxan-2-yl]methyl]-5-methylpyrazine-2-carboxamide -continued

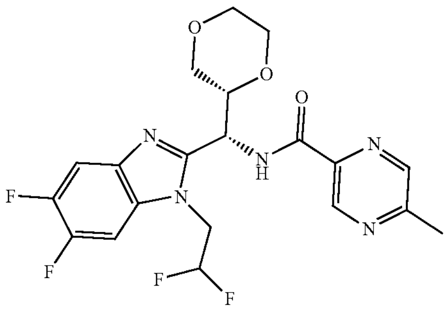 [SMILES: Cc1cnc(C(=O)N[C@H](c2nc3cc(F)c(F)cc3n2CC(F)F)[C@@H]2COCCO2)cn1]

| | |
|---|---|
| HPLC-MS; Method: Z011_S03; $R_t$ [min]: 0.83 | MS: 454 $(M + H)^+$ |
| Chiral SFC Rt Method: I_SZ_15_MEOH_NH3_003 | $R_t$ [min]: 1,481 |
| $^1$H NMR (400 MHz, DMSO-$d_6$) δ ppm-2.57 − 2.61 (m, 3 H) −3.44 − 3.57 (m, 3 H) −3.57 3.77 (m, 2 H) 3.97 (dd, J = 11.28, 2.28 Hz, 1 H) −4.16 − 4.43 (m, 1 H) 4.93 (tt, J = 15.40, 3.36 Hz, 2 H) 5.46 (t, J = 8.87 Hz, 1 H) −6.30 − 6.66 (m, 1 H) 7.76 (br dd, J = 10.90, 7.48 Hz, 1 H) 7.80 (br dd, J = 10.71, 7.29 Hz, 1 H) 8.65 (d, J = 1.14 Hz, 1 H) 9.03 (d, J = 1.39 Hz, 1 H) 9.26 (d, J = 8.62 Hz, 1 H). | |

Examples 10 and 11

The following compounds are obtained in analogy to example 1 (see below) except step 8. In step 8 the product, consisting of 2 stereoisomers, is purified by crystallization resulting in one single stereoisomer.

Synthesis of Example 1

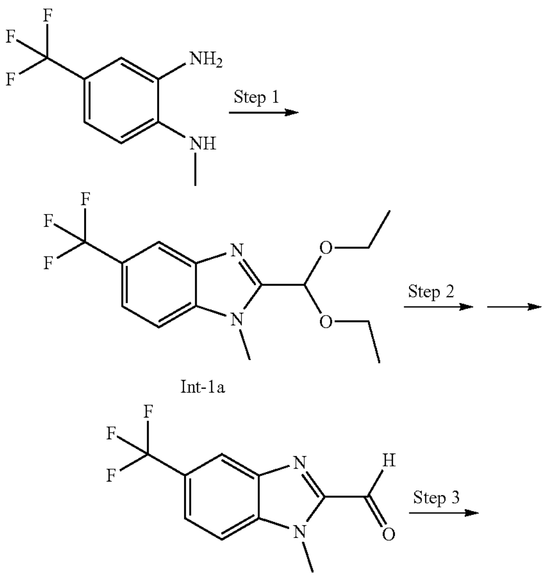

Int-1a

Int-1b

-continued
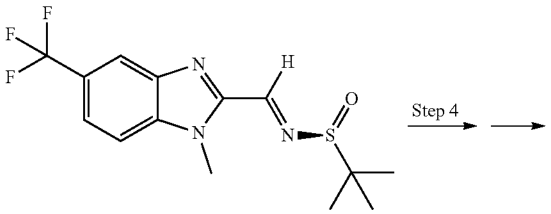
Int-1c
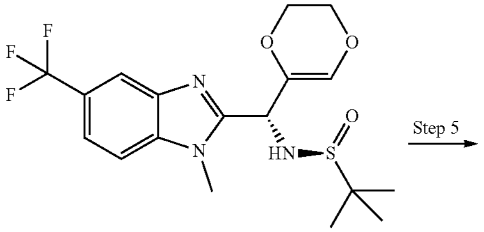
Int-1d
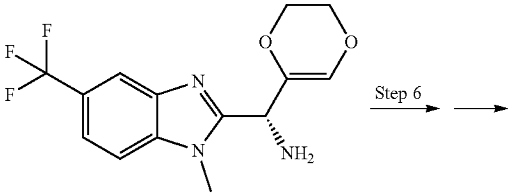
Int-1e
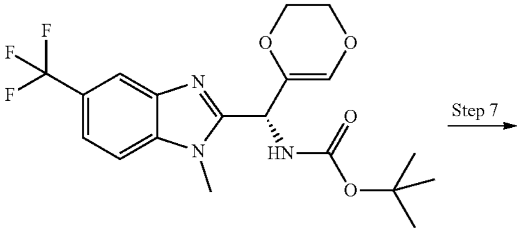
Int-1f
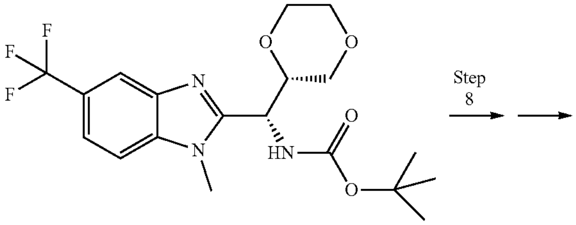
Int-1g
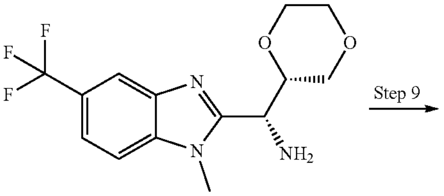
Int-1h
-continued
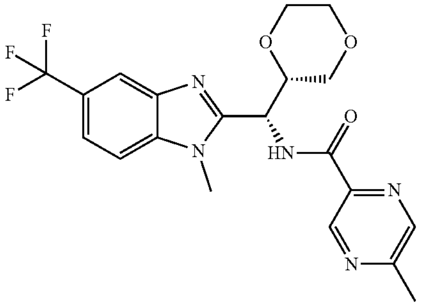
Example 1, 1-1
Example 10 and 11
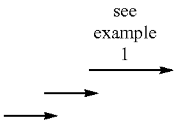
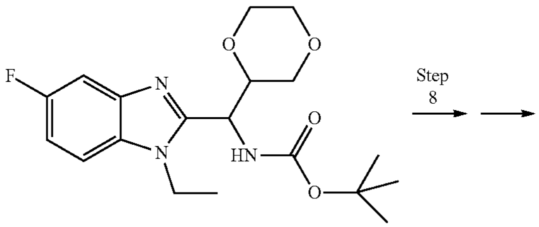
Int-10g
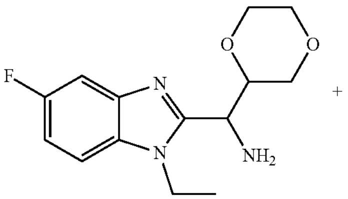
Int-10h
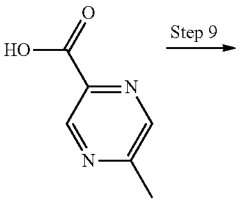
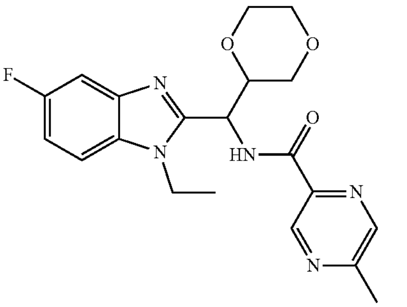
Example 10

Intermediate 10 g was synthesized in analogy to Intermediate 1 g and using as starting material 1,4-difluoro-2-nitrobenzene.

Int-10g: tert-butyl N-[(1,4-dioxan-2-yl)(1-ethyl-5-fluoro-1H-1,3-benzodiazol-2-yl)methyl]carbamate

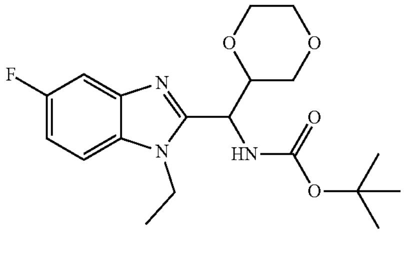 [SMILES: CCn1c(C(NC(=O)OC(C)(C)C)C2COCCO2)nc2cc(F)ccc21]

MS: 380 $(M + H)^+$
Chiral SFC Rt Method: I_SB_05_IPA NH3 002 — Rt [min]: 0.95
$^1$H NMR (400 MHz, DMSO-$d_6$) δ ppm 1.17 - 1.53 (m, 12 H) 3.21 - 3.27 (m, 1 H) 3.39 - 3.53 (m, 1 H) 3.53 - 3.76 (m, 3 H) 3.76 - 3.90 (m, 1 H) 4.02 - 4.22 (m, 1 H) 4.22 - 4.42 (m, 2 H) 4.82 - 5.10 (m, 1 H) 7.10 (t, J = 9.23 Hz, 1 H) 7.37 - 7.48 (m, 2 H) 7.53 - 7.64 (m, 1 H)

Step 8:

TFA (5.083 ml, 65.88 mmol) is added to Int-10 g (2.5 g, 6.589 mmol) in 30 ml DCM at 5° C. Cooling is removed and the mixture stirred for 6.5 h at ambient temperature. DCM (50 ml) is added to the mixture and then water (150 ml) is added. The organic phase is extracted two times with water (100 ml). The combined water phases are adjusted to pH ~10 by addition of conc. aq. $NH_3$ solution. The aqueous layer is extracted with ethyl acetate (250 ml). The combined organic layers are dried over $MgSO_4$ and concentrated i. vac. To the residue (1.67 g) is added ethanol (11.75 ml) and water (0.62 ml). The mixture is heated at 70° C. Then 5-methylpyrazine-2-carboxylic acid (0.775 g, 5.612 mmol) is added. To this mixture ethanol (5.87 ml) and water (0.31 ml) are added and the mixture is heated for 1 hour at 70° C. After that the mixture is slowly cooled to room temperature. The mixture is then cooled within 1 minute to 20° C. The mixture is filtrated, washed with ethanol (3 ml) and dried in a dry gun at 50° C.

Yield: 1.81 g (4.33 mmol; 73%) Int-10 h as a salt with 5-methylpyrazine-2-carboxylic acid Step 9:

A mixture of Int-10 h as a salt with 5-methylpyrazine-2-carboxylic acid (0.55 g, 1.32 mmol), NMM (0.581 mL, 5.27 mmol) in 5.5 ml EtOAc and 5-methylpyraine-2-carboxylic acid (90.9 mg, 0.66 mmol) is cooled to 0° C. under stirring. Then PPA (50% in EtOAc; 1.165 mL, 1.97 mmol) is added. Cooling is removed after 10 min and the mixture stirred at ambient temperature for 45 min. Ethyl acetate (20 ml) is added to the mixture, which is then extracted two times sodium bicarbonate solution. The combined organic phases are dried over $MgSO_4$. After filtration the mixture is concentrated i. vac., the residue taken up in THF/MeOH and purified via chromatography (XBridge C18, 10, ($H_2O$+0.1% NH4OH+28-48% ACN). The product containing fractions are combined and concentrated i. vac. The product is obtained as a single stereoisomer.

Yield: 0.461 mg (1.15 mmol; 87%) example 10.

Example 10: N-[(1,4-dioxan-2-yl)(1-ethyl-5-fluoro-1H-1,3-benzodiazol-2-yl)methyl]-5-methylpyrazine-2-carboxamide

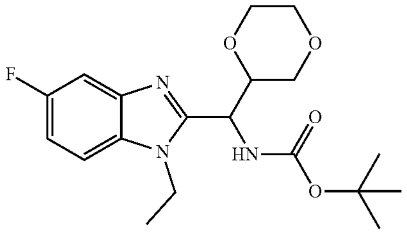 [SMILES: CCn1c(C(NC(=O)OC(C)(C)C)C2COCCO2)nc2cc(F)ccc21]

HPLC-MS; Method: Z011_S03; $R_t$ [min]: 0.89 — MS: 400 $(M + H)^+$
Chiral SFC Rt Method: I_SC_20_IPA_NH3_003 — Rt [min]: 3,59
$^1$H NMR (400 MHz, DMSO-$d_6$) δ ppm 1.31 (t, J = 7.16 Hz, 3 H) 2.60 (s, 3 H) 3.32 - 3.42 (m, 1 H) 3.42 - 3.57 (m, 1 H) 3.57 - 3.73 (m, 2 H) 3.73 - 3.84 (m, 2 H) 4.28 - 4.36 (m, 1 H) 4.36 - 4.50 (m, 2 H) 5.59 (dd, J = 8.36, 7.22 Hz, 1 H) 7.13 (ddd, J = 9.70, 8.87, 2.47 Hz, 1 H) 7.46 (dd, J = 9.76, 2.41 Hz, 1 H) 7.62 (dd, J = 8.87, 4.69 Hz, 1 H) 8.66 (d, J = 1.01 Hz, 1 H) 9.04 (d, J = 8.49 Hz, 1 H) 9.07 (d, J = 1.39 Hz, 1 H)

In analogy to example 10 the following compound, example 11, is obtained.

Intermediate 11 g was synthesized in analogy to Intermediate 1 g and using as starting material 1,2,4-trifluoro-5-nitrobenzene.

Int-11g: tert-butyl N-[(1,4-dioxan-2-yl)(1-ethyl-5,6-difluoro-1H-1,3-benzodiazol-2-yl)methyl]carbamate

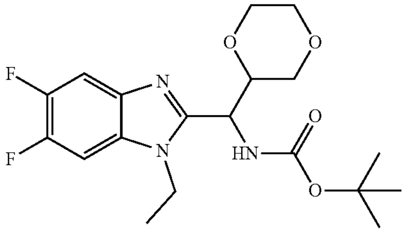 [SMILES: CCn1c(C(NC(=O)OC(C)(C)C)C2COCCO2)nc2cc(F)c(F)cc21]

HPLC-MS; Method: Z018_S04; $R_t$ [min]: 0.73 — MS: 298 $(M + H)^+$
Chiral SFC Rt Method: I_IG_10_MEOH_NH3 002 — Rt [min]: 0.739
$^1$H NMR (400 MHz, DMSO-$d_6$) δ ppm 1.24 - 1.42 (m, 12 H) 3.17 - 3.29 (m, 1 H) 3.36 - 3.54 (m, 1 H) 3.54 - 3.76 (m, 3 H) 3.76 - 3.88 (m, 1 H) 4.02 - 4.23 (m, 1 H) 4.23 - 4.39 (m, 2 H) 4.81 - 5.09 (m, 1 H) 7.46 (br d, J = 8.62 Hz, 1 H) 7.63 - 7.71 (m, 1 H) 7.77 (t, J = 9.01 Hz, 1 H)

Example 11: N-[(1,4-dioxan-2-yl)(1-ethyl-5-fluoro-1H-1,3-benzodiazol-2-yl)methyl]-5-methylpyrazine-2-carboxamide

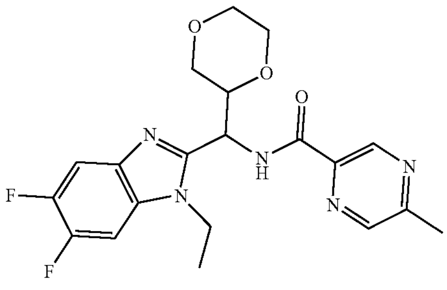 [SMILES: CCn1c(C(NC(=O)c2cnc(C)cn2)C2COCCO2)nc2cc(F)c(F)cc21]

-continued
| | |
|---|---|
| HPLC-MS; Method: Z011_S03; $R_t$ [min]: 0.92 | MS: 418 (M + H)$^+$ |
| Chiral SFC Rt Method: I_SB_10_MEOH_NH3_003 | Rt [min]: 2,39 |
| $^1$H NMR (400 MHz, DMSO-$d_6$) δ ppm 1.29 (t, J = 7.16 Hz, 3 H) 2.60 (s, 3 H) 3.32 - 3.41 (m, 1 H) 3.41 - 3.55 (m, 1 H) 3.55 - 3.71 (m, 2 H) 3.71 - 3.84 (m, 2 H) 4.27 - 4.48 (m, 3 H) 5.58 (dd, J = 8.49, 7.22 Hz, 1 H) 7.72 (dd, J = 11.03, 7.48 Hz, 1 H) 7.81 (dd, J = 10.77, 7.35 Hz, 1 H) 8.65 (d, J = 1.01 Hz, 1 H) 9.04 (d, J = 8.49 Hz, 1 H) 9.06 (d, J = 1.27 Hz, 1 H) | |
The invention claimed is:
1. A compound selected from the group consisting of
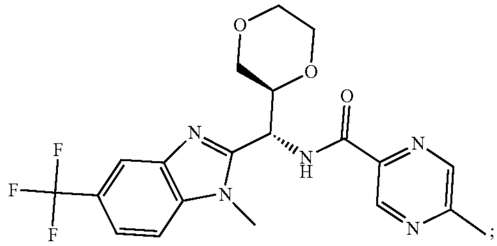
;
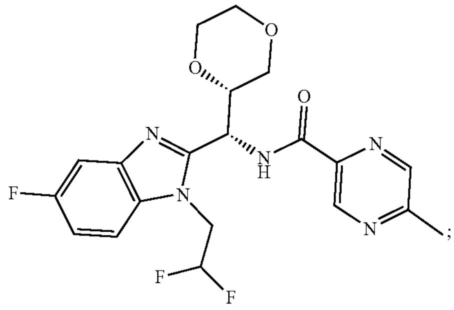
;
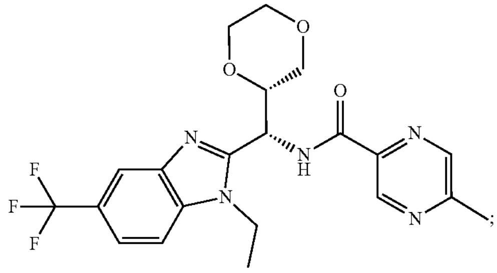
;
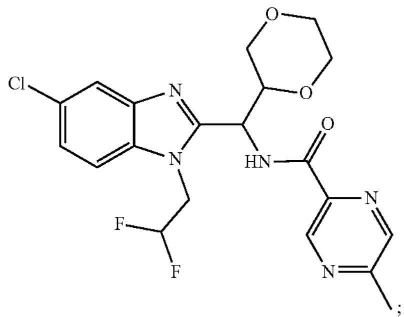
;
-continued
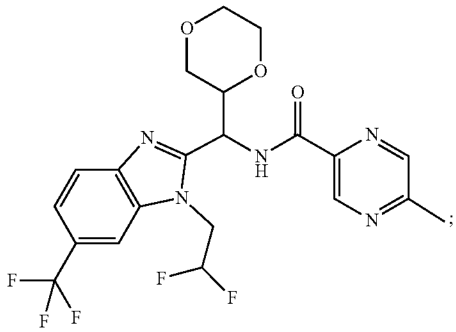
;
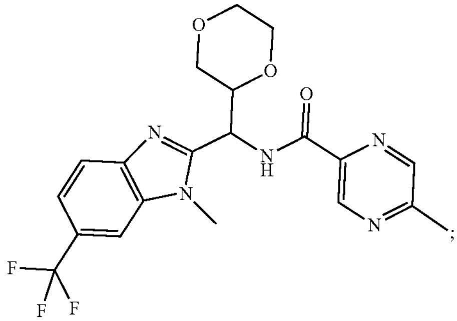
;
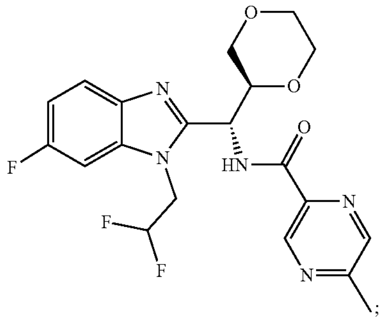
;
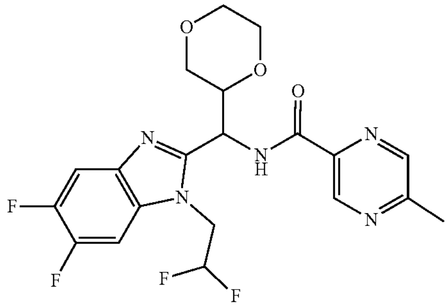
;
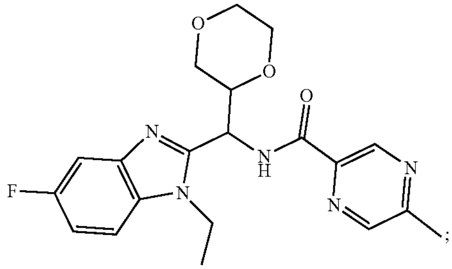
; and -continued

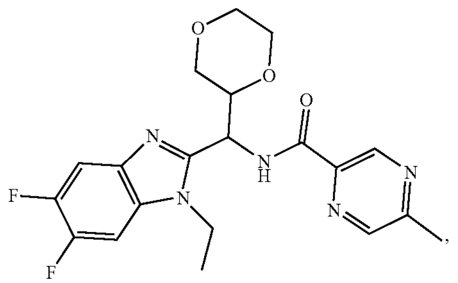

and the pharmaceutically acceptable salts thereof.

2. A pharmaceutically acceptable salt of the compound according to claim 1.

3. A pharmaceutical composition comprising the compound according to claim 1, or a pharmaceutically acceptable thereof.

4. A compound having the structure:

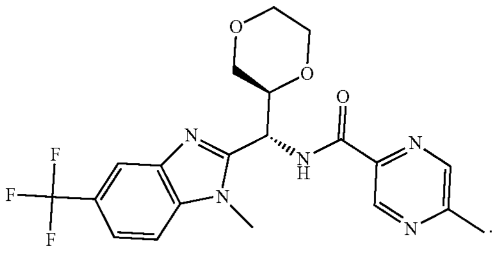 [SMILES: Cc1cnc(C(=O)N[C@H](c2nc3cc(C(F)(F)F)ccc3n2C)[C@H]2COCCO2)cn1]

5. A compound having the structure:

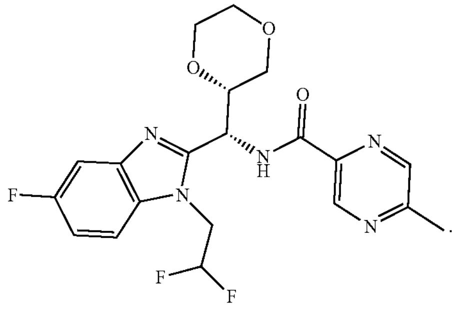 [SMILES: Cc1cnc(C(=O)N[C@H](c2nc3cc(F)ccc3n2CC(F)F)[C@H]2COCCO2)cn1]

6. A compound having the structure:

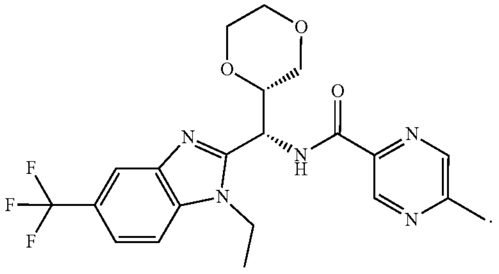 [SMILES: CCn1c([C@@H](NC(=O)c2cnc(C)cn2)[C@H]2COCCO2)nc2cc(C(F)(F)F)ccc21]

7. A compound having the structure:

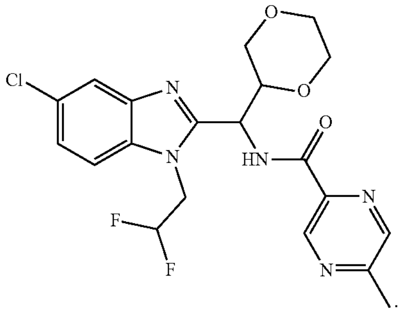 [SMILES: Cc1cnc(C(=O)NC(c2nc3cc(Cl)ccc3n2CC(F)F)C2COCCO2)cn1]

8. A compound having the structure:

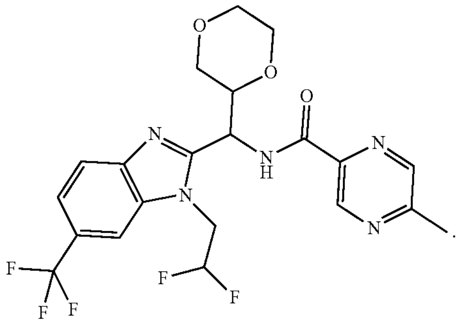 [SMILES: Cc1cnc(C(=O)NC(c2nc3ccc(C(F)(F)F)cc3n2CC(F)F)C2COCCO2)cn1]

9. A compound having the structure:

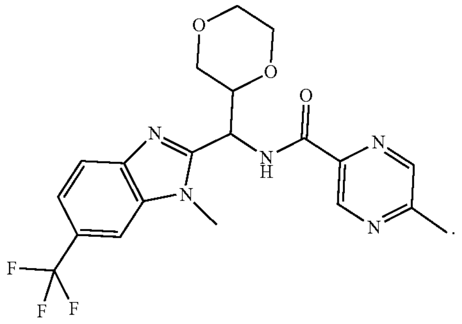 [SMILES: Cc1cnc(C(=O)NC(c2nc3ccc(C(F)(F)F)cc3n2C)C2COCCO2)cn1]

10. A compound having the structure:

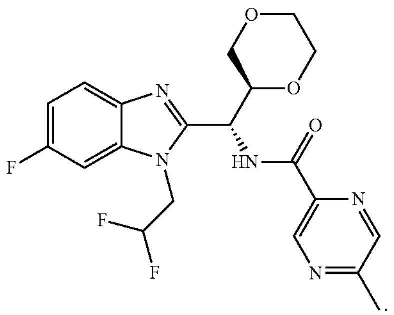 [SMILES: Cc1cnc(C(=O)N[C@H](c2nc3ccc(F)cc3n2CC(F)F)[C@H]2COCCO2)cn1]

11. A compound having the structure:

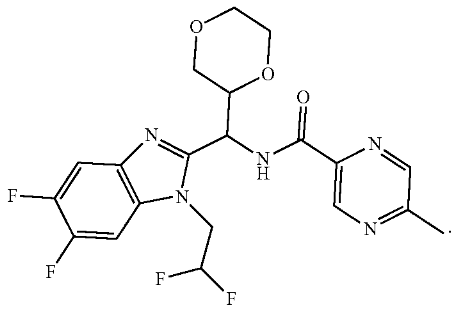 [SMILES: Cc1cnc(C(=O)NC(c2nc3cc(F)c(F)cc3n2CC(F)F)C2COCCO2)cn1]

12. A compound having the structure:

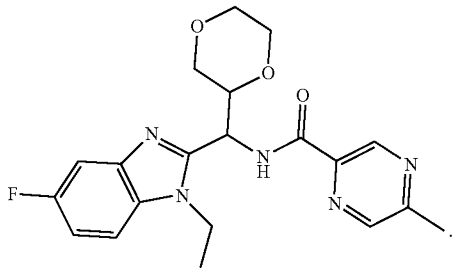 [SMILES: CCn1c(C(NC(=O)c2cnc(C)cn2)C2COCCO2)nc2cc(F)ccc21]

13. A compound having the structure:

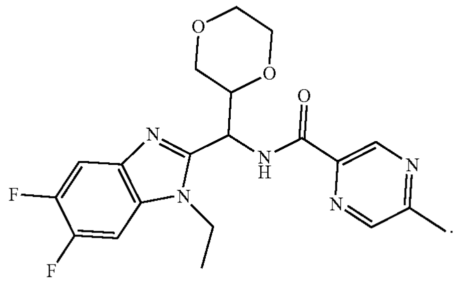 [SMILES: CCn1c(C(NC(=O)c2cnc(C)cn2)C2COCCO2)nc2cc(F)c(F)cc21]

14. A pharmaceutical composition comprising the compound according to claim 4.

15. A pharmaceutical composition comprising the compound according to claim 5.

16. A pharmaceutical composition comprising the compound according to claim 6.

17. A pharmaceutical composition comprising the compound according to claim 7.

18. A pharmaceutical composition comprising the compound according to claim 8.

19. A pharmaceutical composition comprising the compound according to claim 9.

20. A pharmaceutical composition comprising the compound according to claim 10.

21. A pharmaceutical composition comprising the compound according to claim 11.

22. A pharmaceutical composition comprising the compound according to claim 12.

23. A pharmaceutical composition comprising the compound according to claim 13.

* * * * *